(12) United States Patent
Hall et al.

(10) Patent No.: US 10,913,779 B2
(45) Date of Patent: Feb. 9, 2021

(54) EXPOSED COLLAGEN-TARGETED FUSION CYTOKINE FOR IMMUNE MODULATION IN INVASIVE CANCERS AND LESIONS OF INFECTIONS

(71) Applicant: Counterpoint Biomedica LLC, Santa Monica, CA (US)

(72) Inventors: Frederick L. Hall, Laguna Niguel, CA (US); Erlinda M. Gordon, Carmel, CA (US)

(73) Assignee: Counterpoint Biomedica LLC, Santa Monica, CA (US)

( * ) Notice: Subject to any disclaimer, the term of this patent is extended or adjusted under 35 U.S.C. 154(b) by 4 days.

(21) Appl. No.: 15/880,434

(22) Filed: Jan. 25, 2018

(65) Prior Publication Data

US 2018/0222959 A1    Aug. 9, 2018

Related U.S. Application Data

(60) Provisional application No. 62/450,416, filed on Jan. 25, 2017.

(51) Int. Cl.

| | |
|---|---|
| *A61K 38/22* | (2006.01) |
| *C07K 14/535* | (2006.01) |
| *C07K 14/755* | (2006.01) |
| *A61K 38/37* | (2006.01) |
| *A61K 38/19* | (2006.01) |
| *C12N 15/85* | (2006.01) |
| *C07K 14/55* | (2006.01) |
| *C07K 14/56* | (2006.01) |
| *C07K 14/52* | (2006.01) |
| *C07K 14/78* | (2006.01) |

(52) U.S. Cl.
CPC .......... *C07K 14/535* (2013.01); *A61K 38/193* (2013.01); *A61K 38/37* (2013.01); *C07K 14/52* (2013.01); *C07K 14/55* (2013.01); *C07K 14/56* (2013.01); *C07K 14/755* (2013.01); *C07K 14/78* (2013.01); *C12N 15/85* (2013.01); *C07K 2319/01* (2013.01); *C07K 2319/02* (2013.01); *C07K 2319/21* (2013.01); *C07K 2319/33* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 6,387,663 B1 | 5/2002 | Hall et al. | |
| 6,468,798 B1 | 10/2002 | Debs et al. | |
| 6,955,898 B2 | 10/2005 | Hall et al. | |
| 2009/0093407 A1* | 4/2009 | Hall | C07K 14/485 |
| | | | 514/8.8 |

FOREIGN PATENT DOCUMENTS

WO    WO 2016/054107    4/2016

OTHER PUBLICATIONS

Arellano et al., "Clinical uses of GM-CSF, a critical appraisal and update." Biologics: Targets & Therapy, Mar. 2008, 2(1):13-27.
Cebon et al., "Granulocyte-macrophage colony stimulating factor from human lymphocytes. The effect of glycosylation on receptor binding and biological activity." J. Biol. Chem. Mar. 15, 1990, 265(8):4483-4491.
Chawla et al., "Advanced phase I/II studies of targeted gene delivery in vivo: intravenous Rexin-G for gemcitabine-resistant metastatic pancreatic cancer." Molecular Therapy, Feb. 1, 2010, 18(2):435-41.
Chawla et al., "Phase I/II and phase II studies of targeted gene delivery in vivo: intravenous Rexin-G for chemotherapy-resistant sarcoma and osteosarcoma." Molecular Therapy. Sep. 1, 2009, Mol Ther 17(9):1651-7.
Colberre-Garapin, et al., "A new dominant hybrid selective marker for higher eukaryotic cells," J. Mol. Biol., Jul. 25, 1981, 150(1):1-4.
Cruz MA, "Interaction of the von Willebrand factor (vWF) with collagen Localization of the primary collagen-binding site by analysis of recombinant vWF a domain polypeptides." Journal of Biological Chemistry, May 5, 1995, 270(18):10822-7.
Fang et al., "Targeting the Tumor Microenvironment: From Understanding Pathways to Effective Clinical Trials." Cancer Res., Aug. 15, 2013, 73:4965-4977.
Ginsburg et al., "Molecular genetics of von Willebrand disease." Blood. May 15, 1999, 79(10):2507-19.
Gordon et al., "Capture and Expansion of Bone Marrow-Derived Mesenchymal Progenitor Cells with a Transforming Growth Factor-β 1-von Willebrand's Factor Fusion Protein for Retrovirus-Mediated Delivery of Coagulation Factor IX." Human gene therapy, Jul. 20, 1997, 8(11):1385-94.
Gordon et al., "Inhibition of metastatic tumor growth in nude mice by portal vein infusions of matrix-targeted retroviral vectors bearing a cytocidal cyclin G1 construct." Cancer research, Jul. 1, 2000, 60:3343-3347, 2000.

(Continued)

*Primary Examiner* — Michael D Pak
(74) *Attorney, Agent, or Firm* — Fish & Richardson P.C.

(57) ABSTRACT

Provided herein are new compositions and methods to target pharmaceutical agents to pathological areas by utilizing fusion polypeptides. These fusion polypeptides contain two or more domains: (i) aptamer sequences that bind to exposed collagenous (XC-) proteins present in pathological areas, including cancerous and viral lesions, (ii) immunomodulators, such as cytokines, and optionally (iii) at least one linker joining the two domains or at the terminus of the polypeptide. In some cases, the linker is a rigid linker, e.g., a rigid helical linker. Also provided herein are methods of treating cancer and/or infectious diseases using the new fusion polypeptides.

21 Claims, 5 Drawing Sheets
Specification includes a Sequence Listing.

(56) References Cited

OTHER PUBLICATIONS

Gordon et al., "Noteworthy clinical case studies in cancer gene therapy: tumor-targeted Rexin-G advances as an efficacious anticancer agent. International journal of oncology," Int'l J Oncol, Jun. 1, 2010, 36:1341-1353.

Gordon et al., "Rexin-G, a targeted genetic medicine for cancer." Expert opinion on biological therapy, May 1, 2010, 10(5):819-32.

Hall et al., "Design, expression, and renaturation of a lesion-targeted recombinant epidermal growth factor—von Willebrand factor fusion protein: efficacy in an animal model of experimental colitis." International journal of molecular medicine. Dec. 1, 2000, 6(6):635-78.

Hall et al., "Molecular engineering of matrix-targeted retroviral vectors incorporating a surveillance function inherent in von Willebrand factor." Human gene therapy, May 1, 2000, 11(7):983-93.

Hall, "Counterpoint Biomedica Lesion Targeted Cytokines," Centerpoint Biomedica, LLC, Dec. 9, 2016, 11 pages.

Hall, "R&D Progress Report," Counterpoint Biomedica, Jun. 30, 2017, 2 pages.

Hartman et al., "Two dominant-acting selectable markers for gene transfer studies in mammalian cells." Proceedings of the National Academy of Sciences. 1988 Nov. 1, 1988, 85(21):8047-51.

Hoylaerts et al., "von Willebrand factor binds to native collagen VI primarily via its A1 domain." Biochemical Journal. May 15, 1997, 324(1):185-91.

Invitrogen by Thermo Fisher Scientific, "Your GeneOptimizer Assisted Sequence Analysis," Jan. 23, 2017, 4 pages.

Jager et al., "Granulocyte-macrophage-colonystimulating factor enhances immune responses to melanoma-associated peptides in vivo." Int. J Cancer, Jul. 3, 1996, 67:54-62.

Lankhof et al., "A3 domain is essential for interaction of von Willebrand factor with collagen type III." Thrombosis and haemostasis. Dec. 1996, 76(6):950-8.

Lee et al., "Cytokines in cancer immunotherapy." Cancers. Oct. 13, 2011, 3(4):3856-93.

Lowy et al., "Isolation of transforming DNA: cloning the hamster aprt gene." Cell, Dec. 1, 1980, 22(3):817-823.

Marini et al., "Recombinant human granulocyte-macrophage colony-stimulating factor: effect of glycosylation on pharmacokinetic parameters." Electronic Journal of Biotechnology, Apr. 15, 2007, 10(2):271-8.

Mulligan et al., "Selection for animal cells that express the *Escherichia coli* gene coding for xanthine-guanine phosphoribosyltransferase." Proceedings of the National Academy of Sciences, Apr. 1, 1981, 78(4):2072-6.

O'Hare, et al, "Transformation of mouse fibroblasts to methotrexate resistance by a recombinant plasmid expressing a prokaryotic dihydrofolate reductase." Proceedings of the National Academy of Sciences. Mar. 1, 1981, 78(3):1527-31.

Ridolfi et al., "Intralesional granulocyte-monocyte colony-stimulating factor followed by subcutaneous interleukin-2 in metastatic melanoma: a pilot study in elderly patients." Journal of the European Academy of Dermatology and Venereology. May 2001, 15(3):218-223.

Ruef et al., "Granulocyte-macrophage colony-stimulating factor: pleiotropic cytokine with potential clinical usefulness." Rev Infect Dis. Jan. 1, 1990, 12(1):41-62.

Santerre, et al., "Expression of prokaryotic genes for hygromycin B and G418 resistance as dominant-selection markers in mouse L cells." Gene. Oct. 31, 1984, 30(1):147-156.

Sounni et al., "Targeting the tumor microenvironment for cancer therapy." Clinical chemistry, Jan. 1, 2013, 59(1):85-93.

Szybalska et al., "Genetics of human cell lines, IV. DNA-mediated heritable transformation of a biochemical trait." Proceedings of the National Academy of Sciences. Dec. 1, 1962, 48(12):2026-34.

Takagi et al., "A Collagen/gelatin-binding decapeptide derived from bovine propolypeptide ofvon Willebrand Factor." Biochemistry, 1992, 31:8530-8534.

Tuan et al., "Engineering, expression and renaturation of targeted TGF-beta fusion proteins." Connective tissue research, Jan. 1, 1996, 34(1):1-9.

Wagner, "Cell biology of von Willebrand factor." Annual review of cell biology, Nov. 1990, 6(1):217-42.

Wigler, et al., "Transfer of purified herpes virus thymidine kinase gene to cultured mouse cells." Cell, May 1, 1977, 11(1):223-32.

Wigler, et al., "Transformation of mammalian cells with an amplifiable dominant-acting gene." Proceedings of the National Academy of Sciences, Jun. 1, 1980, 77(6):3567-70.

Yuzhakova et al., "Immunotherapy of Cancer (Review)" CTM 2016; vol. 8:(1):173-181.

Zhang et al., "Synthesis of granulocyte—macrophage colony-stimulating factor as homogeneous glycoforms and early comparisons with yeast cell-derived material." Proceedings of the National Academy of Sciences, Feb. 25, 2014, 111(8):2885-90.

\* cited by examiner

SEQUENCE LISTING

<160> NUMBER OF SEQ ID NOS: 40

<210> SEQ ID NO 1
<211> LENGTH: 24
<212> TYPE: PRT
<213> ORGANISM: Artificial Sequence
<220> FEATURE:
<223> OTHER INFORMATION: XC domain optimized for construct

<400> SEQUENCE: 1

Ala Arg Arg Gly Val Arg Val Ala Trp Arg Glu Pro Gly Arg Met Glu
1               5                   10                  15

Leu Asn Met Pro His Gly Gln Glu
            20

<210> SEQ ID NO 2
<211> LENGTH: 120
<212> TYPE: PRT
<213> ORGANISM: Homo sapiens
<220> FEATURE:
<221> NAME/KEY: MISC_FEATURE
<223> OTHER INFORMATION: vWFpp collagen binding domain D2

<400> SEQUENCE: 2

Pro Leu Pro Tyr Leu Arg Asn Cys Arg Tyr Asp Val Cys Ser Cys Ser
1               5                   10                  15

Asp Gly Arg Glu Cys Leu Cys Gly Ala Leu Ala Ser Tyr Ala Ala Ala
            20                  25                  30

Cys Ala Gly Arg Gly Val Arg Val Ala Trp Arg Glu Pro Gly Arg Cys
        35                  40                  45

Glu Leu Asn Cys Pro Lys Gly Gln Val Tyr Leu Gln Cys Gly Thr Pro
    50                  55                  60

Cys Asn Leu Thr Cys Arg Ser Leu Ser Tyr Pro Asp Glu Glu Cys Asn
65                  70                  75                  80

Glu Ala Cys Leu Glu Gly Cys Phe Cys Pro Pro Gly Leu Tyr Met Asp
                85                  90                  95

Glu Arg Gly Asp Cys Val Pro Lys Ala Gln Cys Pro Cys Tyr Tyr Asp
            100                 105                 110

Gly Glu Ile Phe Gln Pro Glu Asp
        115                 120

<210> SEQ ID NO 3
<211> LENGTH: 120
<212> TYPE: PRT
<213> ORGANISM: Bos taurus

<400> SEQUENCE: 3

Ile Leu Thr Ser Pro Lys Phe Glu Ala Cys His Ser Ala Val Ser Pro
1               5                   10                  15

Leu Pro Tyr Leu Arg Asn Cys Arg Tyr Asp Val Cys Ala Cys Ser Asp
            20                  25                  30

Gly Arg Asp Cys Leu Cys Asp Ala Val Ala Asn Tyr Ala Ala Ala Cys
        35                  40                  45

Ala Arg Arg Gly Val His Val Gly Trp Arg Glu Pro Ser Phe Cys Ala
    50                  55                  60

Leu Ser Cys Thr His Gly Gln Val Tyr Gln Gln Cys Gly Thr Pro Cys
65                  70                  75                  80

Asn Leu Thr Cys Arg Ser Leu Ser His Pro Asp Glu Glu Cys Thr Glu
                85                  90                  95

```
Val Cys Leu Glu Gly Cys Phe Cys Pro Pro Gly Leu Phe Leu Asp Glu
            100                 105                 110

Thr Gly Ser Cys Val Pro Lys Ala
        115                 120

<210> SEQ ID NO 4
<211> LENGTH: 23
<212> TYPE: PRT
<213> ORGANISM: Homo sapiens

<400> SEQUENCE: 4

Cys Ala Gly Arg Gly Val Arg Val Ala Trp Arg Glu Pro Gly Arg Cys
1               5                   10                  15

Glu Leu Asn Cys Pro Lys Gly
            20

<210> SEQ ID NO 5
<211> LENGTH: 23
<212> TYPE: PRT
<213> ORGANISM: Bos taurus

<400> SEQUENCE: 5

Cys Ala Arg Arg Gly Val His Val Gly Trp Arg Glu Pro Ser Phe Cys
1               5                   10                  15

Ala Leu Ser Cys Pro His Gly
            20

<210> SEQ ID NO 6
<211> LENGTH: 23
<212> TYPE: PRT
<213> ORGANISM: Artificial Sequence
<220> FEATURE:
<223> OTHER INFORMATION: XC domain hybrid

<400> SEQUENCE: 6

Cys Ala Arg Arg Gly Val His Val Gly Trp Arg Glu Pro Gly Arg Met
1               5                   10                  15

Glu Leu Asn Met Pro His Gly
            20

<210> SEQ ID NO 7
<211> LENGTH: 10
<212> TYPE: PRT
<213> ORGANISM: Artificial Sequence
<220> FEATURE:
<223> OTHER INFORMATION: XC domain

<400> SEQUENCE: 7

Trp Arg Glu Pro Ser Phe Met Ala Leu Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: XC domain

<400> SEQUENCE: 8

Trp Arg Glu Pro Gly Arg Met Glu Leu Asn
1               5                   10

<210> SEQ ID NO 9
<211> LENGTH: 14
```

```
<212> TYPE: PRT
<213> ORGANISM: Artificial Sequence
<220> FEATURE:
<223> OTHER INFORMATION: XC domain rigid helical

<400> SEQUENCE: 9

Gly Ala Glu Ala Ala Ala Lys Glu Ala Ala Ala Lys Ala Gly
1               5                   10

<210> SEQ ID NO 10
<211> LENGTH: 12
<212> TYPE: PRT
<213> ORGANISM: Artificial Sequence
<220> FEATURE:
<223> OTHER INFORMATION: XC domain helical

<400> SEQUENCE: 10

Ala Glu Ala Ala Ala Lys Glu Ala Ala Ala Lys Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: XC domain flexible linker

<400> SEQUENCE: 11

Gly Ser Ala Gly Ser Ala Ala Gly Ser Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: XC domain GLY, SER-RICH

<400> SEQUENCE: 12

Gly Ser Ala Gly Ser Ala Ala Gly Ser Gly Glu Phe
1               5                   10

<210> SEQ ID NO 13
<211> LENGTH: 9
<212> TYPE: PRT
<213> ORGANISM: Artificial Sequence
<220> FEATURE:
<223> OTHER INFORMATION: XC domain GLY, SER-RICH

<400> SEQUENCE: 13

Gly Ser Ala Gly Ser Ala Ala Gly Ser
1               5

<210> SEQ ID NO 14
<211> LENGTH: 127
<212> TYPE: PRT
<213> ORGANISM: Homo sapiens

<400> SEQUENCE: 14

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45
```

Leu Gln Glu Pro Thr Cys Leu Gln Thr Arg Leu Glu Leu Tyr Lys Gln
            50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu
            115                 120                 125

<210> SEQ ID NO 15
<211> LENGTH: 17
<212> TYPE: PRT
<213> ORGANISM: Artificial Sequence
<220> FEATURE:
<223> OTHER INFORMATION: HIS-Tag with protease site

<400> SEQUENCE: 15

His His His His His His His His Glu Asn Leu Tyr Phe Gln
 1               5                  10                  15

Gly

<210> SEQ ID NO 16
<211> LENGTH: 20
<212> TYPE: PRT
<213> ORGANISM: Mus musculus

<400> SEQUENCE: 16

Met Glu Thr Asp Thr Leu Leu Leu Trp Val Leu Leu Leu Trp Val Pro
 1               5                  10                  15

Gly Ser Thr Gly
            20

<210> SEQ ID NO 17
<211> LENGTH: 165
<212> TYPE: PRT
<213> ORGANISM: Artificial Sequence
<220> FEATURE:
<223> OTHER INFORMATION: GM-CSF + Helical Linker + XC-binding

<400> SEQUENCE: 17

Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu Gly
            115                 120                 125

Ala Glu Ala Ala Ala Lys Glu Ala Ala Ala Lys Ala Gly Ala Arg Arg

```
                    130                 135                 140
Gly Val Arg Val Ala Trp Arg Glu Pro Gly Arg Met Glu Leu Asn Met
145                 150                 155                 160

Pro His Gly Gln Glu
                165

<210> SEQ ID NO 18
<211> LENGTH: 161
<212> TYPE: PRT
<213> ORGANISM: Artificial Sequence
<220> FEATURE:
<223> OTHER INFORMATION: GM-CSF + Flexible Linker + XC-binding

<400> SEQUENCE: 18

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu Gly
            115                 120                 125

Ser Ala Gly Ser Ala Ala Gly Ser Gly Ala Arg Arg Gly Val Arg Val
        130                 135                 140

Ala Trp Arg Glu Pro Gly Arg Met Glu Leu Asn Met Pro His Gly Gln
145                 150                 155                 160

Glu

<210> SEQ ID NO 19
<211> LENGTH: 202
<212> TYPE: PRT
<213> ORGANISM: Artificial Sequence
<220> FEATURE:
<223> OTHER INFORMATION: Signal Peptide + His-Tag w/ Protease Site +
      GM-CSF + Helical Linker + XC-binding

<400> SEQUENCE: 19

Met Glu Thr Asp Thr Leu Leu Leu Trp Val Leu Leu Leu Trp Val Pro
1               5                   10                  15

Gly Ser Thr Gly His His His His His His His His Glu Asn
                20                  25                  30

Leu Tyr Phe Gln Gly Ala Pro Ala Arg Ser Pro Ser Pro Ser Thr Gln
            35                  40                  45

Pro Trp Glu His Val Asn Ala Ile Gln Glu Ala Arg Arg Leu Leu Asn
        50                  55                  60

Leu Ser Arg Asp Thr Ala Ala Glu Met Asn Glu Thr Val Glu Val Ile
65                  70                  75                  80

Ser Glu Met Phe Asp Leu Gln Glu Pro Thr Cys Leu Gln Thr Arg Leu
                85                  90                  95
```

```
Glu Leu Tyr Lys Gln Gly Leu Arg Gly Ser Leu Thr Lys Leu Lys Gly
            100                 105                 110

Pro Leu Thr Met Met Ala Ser His Tyr Lys Gln His Cys Pro Pro Thr
            115                 120                 125

Pro Glu Thr Ser Cys Ala Thr Gln Ile Ile Thr Phe Glu Ser Phe Lys
        130                 135                 140

Glu Asn Leu Lys Asp Phe Leu Leu Val Ile Pro Phe Asp Cys Trp Glu
145                 150                 155                 160

Pro Val Gln Glu Gly Ala Glu Ala Ala Lys Glu Ala Ala Lys
                    165                 170                 175

Ala Gly Ala Arg Arg Gly Val Arg Val Ala Trp Arg Glu Pro Gly Arg
            180                 185                 190

Met Glu Leu Asn Met Pro His Gly Gln Glu
            195                 200

<210> SEQ ID NO 20
<211> LENGTH: 4
<212> TYPE: PRT
<213> ORGANISM: Artificial Sequence
<220> FEATURE:
<223> OTHER INFORMATION: Linker

<400> SEQUENCE: 20

Gly Gly Ser Gly
1

<210> SEQ ID NO 21
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: MOD_RES
<222> LOCATION: (1)..(2)
<223> OTHER INFORMATION: D-Arg

<400> SEQUENCE: 21

Arg Arg Gly Val His Val Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Linker

<400> SEQUENCE: 22

Gly Gly Ser Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Linker

<400> SEQUENCE: 23

Ser Gly Gly Ser Gly
1               5

<210> SEQ ID NO 24
```

```
<211> LENGTH: 6
<212> TYPE: PRT
<213> ORGANISM: Artificial Sequence
<220> FEATURE:
<223> OTHER INFORMATION: Linker

<400> SEQUENCE: 24

Gly Ser Gly Ser Gly Ser
1               5

<210> SEQ ID NO 25
<211> LENGTH: 7
<212> TYPE: PRT
<213> ORGANISM: Artificial Sequence
<220> FEATURE:
<223> OTHER INFORMATION: Linker

<400> SEQUENCE: 25

Gly Gly Ser Gly Gly Ser Lys
1               5

<210> SEQ ID NO 26
<211> LENGTH: 9
<212> TYPE: PRT
<213> ORGANISM: Artificial Sequence
<220> FEATURE:
<223> OTHER INFORMATION: Linker

<400> SEQUENCE: 26

Gly Ser Gly Gly Ser Gly Gly Ser Gly
1               5

<210> SEQ ID NO 27
<211> LENGTH: 8
<212> TYPE: PRT
<213> ORGANISM: Artificial Sequence
<220> FEATURE:
<223> OTHER INFORMATION: Linker

<400> SEQUENCE: 27

Gly Gly Ser Gly Gly Ser Gly Gly
1               5

<210> SEQ ID NO 28
<211> LENGTH: 4
<212> TYPE: PRT
<213> ORGANISM: Artificial Sequence
<220> FEATURE:
<223> OTHER INFORMATION: Linker

<400> SEQUENCE: 28

Gly Gly Gly Gly
1

<210> SEQ ID NO 29
<211> LENGTH: 127
<212> TYPE: PRT
<213> ORGANISM: Artificial Sequence
<220> FEATURE:
<223> OTHER INFORMATION: HUMAN based VAR 115 T to I

<400> SEQUENCE: 29

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30
```

Ala Ala Glu Met Asn Glu Thr Val Glu Val Ile Ser Glu Met Phe Asp
             35                  40                  45

Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Ile Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 30
<211> LENGTH: 127
<212> TYPE: PRT
<213> ORGANISM: Artificial Sequence
<220> FEATURE:
<223> OTHER INFORMATION: HUMAN based VAR 117 I to T

<400> SEQUENCE: 30

Ala Pro Ala Arg Ser Pro Ser Pro Ser Thr Gln Pro Trp Glu His Val
 1               5                  10                  15

Asn Ala Ile Gln Glu Ala Arg Arg Leu Leu Asn Leu Ser Arg Asp Thr
             20                  25                  30

Ala Ala Glu Met Asn Glu Thr Val Glu Val Ile Ser Glu Met Phe Asp
             35                  40                  45

Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Thr Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 31
<211> LENGTH: 4
<212> TYPE: PRT
<213> ORGANISM: Artificial Sequence
<220> FEATURE:
<223> OTHER INFORMATION: linker from FITC constructs

<400> SEQUENCE: 31

Gly Ser Gly Lys
 1

<210> SEQ ID NO 32
<211> LENGTH: 21
<212> TYPE: PRT
<213> ORGANISM: Artificial Sequence
<220> FEATURE:
<223> OTHER INFORMATION: XC domain from FITC construct

<400> SEQUENCE: 32

Arg Arg Gly Val His Val Gly Trp Arg Glu Pro Ser Phe Met Ala Leu
 1               5                  10                  15

Ser Met Pro His Gly

-continued

20

<210> SEQ ID NO 33
<211> LENGTH: 21
<212> TYPE: PRT
<213> ORGANISM: Artificial Sequence
<220> FEATURE:
<223> OTHER INFORMATION: XC domain from FITC construct

<400> SEQUENCE: 33

Arg Arg Gly Val Arg Val Ala Trp Arg Glu Pro Gly Arg Met Glu Leu
1               5                   10                  15

Asn Met Pro His Gly
            20

<210> SEQ ID NO 34
<211> LENGTH: 25
<212> TYPE: PRT
<213> ORGANISM: Artificial Sequence
<220> FEATURE:
<223> OTHER INFORMATION: Labeled moiety XC-BD-1

<400> SEQUENCE: 34

Arg Arg Gly Val His Val Gly Trp Arg Glu Pro Ser Phe Met Ala Leu
1               5                   10                  15

Ser Met Pro His Gly Gly Ser Gly Lys
            20                  25

<210> SEQ ID NO 35
<211> LENGTH: 25
<212> TYPE: PRT
<213> ORGANISM: Artificial Sequence
<220> FEATURE:
<223> OTHER INFORMATION: Labeled moiety XC-BD-2

<400> SEQUENCE: 35

Arg Arg Gly Val Arg Val Ala Trp Arg Glu Pro Gly Arg Met Glu Leu
1               5                   10                  15

Asn Met Pro His Gly Gly Ser Gly Lys
            20                  25

<210> SEQ ID NO 36
<211> LENGTH: 200
<212> TYPE: PRT
<213> ORGANISM: Artificial Sequence
<220> FEATURE:
<223> OTHER INFORMATION: Signal peptide + His-tag with protease +
      XC-binding domain +rigid helical linker + GM-CSF

<400> SEQUENCE: 36

```
Met Glu Thr Asp Thr Leu Leu Leu Trp Val Leu Leu Leu Trp Val Pro
1               5                   10                  15

Gly Ser Thr Gly His His His His His His His His His His Glu Asn
            20                  25                  30

Leu Tyr Phe Gln Gly Ala Arg Arg Gly Val His Val Gly Trp Arg Glu
        35                  40                  45

Pro Gly Arg Met Glu Leu Asn Met Pro His Gly Gly Ala Glu Ala Ala
    50                  55                  60

Ala Lys Glu Ala Ala Ala Lys Ala Gly Ala Pro Ala Arg Ser Pro Ser
65                  70                  75                  80

Pro Ser Thr Gln Pro Trp Glu His Val Asn Ala Ile Gln Glu Ala Arg
                85                  90                  95
```

```
Arg Leu Leu Asn Leu Ser Arg Asp Thr Ala Ala Glu Met Asn Glu Thr
            100                 105                 110

Val Glu Val Ile Ser Glu Met Phe Asp Leu Gln Glu Pro Thr Cys Leu
        115                 120                 125

Gln Thr Arg Leu Glu Leu Tyr Lys Gln Gly Leu Arg Gly Ser Leu Thr
    130                 135                 140

Lys Leu Lys Gly Pro Leu Thr Met Met Ala Ser His Tyr Lys Gln His
145                 150                 155                 160

Cys Pro Pro Thr Pro Glu Thr Ser Cys Ala Thr Gln Ile Ile Thr Phe
                165                 170                 175

Glu Ser Phe Lys Glu Asn Leu Lys Asp Phe Leu Leu Val Ile Pro Phe
            180                 185                 190

Asp Cys Trp Glu Pro Val Gln Glu
            195                 200

<210> SEQ ID NO 37
<211> LENGTH: 564
<212> TYPE: DNA
<213> ORGANISM: Artificial Sequence
<220> FEATURE:
<223> OTHER INFORMATION: Signal peptide + His-tag with protease +
      XC-binding domain +rigid helical linker + GM-CSF

<400> SEQUENCE: 37
ggcagcaccg gccaccacca tcaccatcac caccatcatc acgagaacct gtattttcaa      60
ggcgccagac ggggcgtgca cgtgggatgg cgggaacccg gcagaatgga actgaacatg     120
ccccacggcg gagccgaggc cgctgccaaa gaagccgctg ctaaagccgg cgctcccgcc     180
agaagcccta gccttctac ccagccctgg gagcacgtga acgccatcca ggaagccaga     240
cggctgctga acctgagccg ggacacagcc gccgagatga acgagacagt ggaagtgatc     300
agcgagatgt tcgatctgca gaacctacc tgcctgcaga cccggctgga actgtacaag     360
cagggcctgc ggggcagcct gaccaagctg aagggccccc tgaccatgat ggccagccac     420
tacaagcagc actgcccccc caccccgag acaagctgcg ccacccagat catcaccttc     480
gagagcttca agagaaacct gaaggacttc ctgctggtga tccccttcga ctgctgggag     540
cccgtgcagg aatgatgaga attc                                            564

<210> SEQ ID NO 38
<211> LENGTH: 20
<212> TYPE: PRT
<213> ORGANISM: Artificial Sequence
<220> FEATURE:
<223> OTHER INFORMATION: XC-binding domain

<400> SEQUENCE: 38

Arg Arg Gly Val His Val Gly Trp Arg Glu Pro Gly Arg Met Glu Leu
1               5                   10                  15

Asn Met Pro His
            20

<210> SEQ ID NO 39
<211> LENGTH: 162
<212> TYPE: PRT
<213> ORGANISM: Artificial Sequence
<220> FEATURE:
<223> OTHER INFORMATION: XC-binding domain +rigid helical linker +
      GM-CSF

<400> SEQUENCE: 39
```

```
Arg Arg Gly Val His Val Gly Trp Arg Glu Pro Gly Arg Met Glu Leu
1               5                   10                  15

Asn Met Pro His Gly Gly Ala Glu Ala Ala Lys Glu Ala Ala Ala
            20                  25                  30

Lys Ala Gly Ala Pro Ala Arg Ser Pro Ser Pro Ser Thr Gln Pro Trp
            35                  40                  45

Glu His Val Asn Ala Ile Gln Glu Ala Arg Arg Leu Leu Asn Leu Ser
    50                  55                  60

Arg Asp Thr Ala Ala Glu Met Asn Glu Thr Val Glu Val Ile Ser Glu
65              70                  75                  80

Met Phe Asp Leu Gln Glu Pro Thr Cys Leu Gln Thr Arg Leu Glu Leu
                85                  90                  95

Tyr Lys Gln Gly Leu Arg Gly Ser Leu Thr Lys Leu Lys Gly Pro Leu
            100                 105                 110

Thr Met Met Ala Ser His Tyr Lys Gln His Cys Pro Pro Thr Pro Glu
            115                 120                 125

Thr Ser Cys Ala Thr Gln Ile Ile Thr Phe Glu Ser Phe Lys Glu Asn
    130                 135                 140

Leu Lys Asp Phe Leu Leu Val Ile Pro Phe Asp Cys Trp Glu Pro Val
145                 150                 155                 160

Gln Glu

<210> SEQ ID NO 40
<211> LENGTH: 198
<212> TYPE: PRT
<213> ORGANISM: Artificial Sequence
<220> FEATURE:
<223> OTHER INFORMATION: Signal Peptide + His-Tag w/ Protease Site +
      GM-CSF + Flexible Linker + XC-binding

<400> SEQUENCE: 40

Met Glu Thr Asp Thr Leu Leu Leu Trp Val Leu Leu Leu Trp Val Pro
1               5                   10                  15

Gly Ser Thr Gly His His His His His His His His Glu Asn
            20                  25                  30

Leu Tyr Phe Gln Gly Ala Pro Ala Arg Ser Pro Ser Pro Ser Thr Gln
            35                  40                  45

Pro Trp Glu His Val Asn Ala Ile Gln Glu Ala Arg Arg Leu Leu Asn
    50                  55                  60

Leu Ser Arg Asp Thr Ala Ala Glu Met Asn Glu Thr Val Glu Val Ile
65              70                  75                  80

Ser Glu Met Phe Asp Leu Gln Glu Pro Thr Cys Leu Gln Thr Arg Leu
                85                  90                  95

Glu Leu Tyr Lys Gln Gly Leu Arg Gly Ser Leu Thr Lys Leu Lys Gly
            100                 105                 110

Pro Leu Thr Met Met Ala Ser His Tyr Lys Gln His Cys Pro Pro Thr
            115                 120                 125

Pro Glu Thr Ser Cys Ala Thr Gln Ile Ile Thr Phe Glu Ser Phe Lys
    130                 135                 140

Glu Asn Leu Lys Asp Phe Leu Leu Val Ile Pro Phe Asp Cys Trp Glu
145                 150                 155                 160

Pro Val Gln Glu Gly Ser Ala Gly Ser Ala Ala Gly Ser Gly Ala Arg
                165                 170                 175
```

-continued

```
Arg Gly Val Arg Val Ala Trp Arg Glu Pro Gly Arg Met Glu Leu Asn
            180                 185                 190
Met Pro His Gly Gln Glu
            195
```

EXPOSED COLLAGEN-TARGETED FUSION CYTOKINE FOR IMMUNE MODULATION IN INVASIVE CANCERS AND LESIONS OF INFECTIONS

CROSS REFERENCE TO RELATED APPLICATION

This application claims priority under 35 USC § 119(e) to U.S. Patent Application Ser. No. 62/450,416, filed on Jan. 25, 2017, the entire contents of which are hereby incorporated by reference.

TECHNICAL FIELD

This invention relates to new compositions and methods capable of selective and efficient targeting of pharmaceutical agents to pathological areas such as cancer and infectious lesions.

BACKGROUND

Cancer is the second most common cause of death in the US, claiming 580,000 Americans per year, more than 1,500 people each day. The chemotherapy market is currently the fastest growing segment of the pharmaceutical industry, with recent estimates topping $50 billion (in 2012) and rising. However, the current therapies, including surgery, systemic chemotherapy, radiation therapy, risk factor modification, are often clinically insufficient and/or unacceptably toxic. The systemic toxicities of many FDA-approved chemotherapeutic agents are a result of the non-specific distribution of these agents in the body, which kills both cancer cells and normal cells and negatively impacts the treatment regimen and patient outcome.

Cytokines such as granulocyte-macrophage colony stimulating factor (GM-CSF) are potent signaling molecules that interact directly with responsive cells of the immune system to generate coordinated, robust albeit self-limited responses to target antigens—which may be either tumor antigens, viral, bacterial, or fungal antigens. Recombinant GM-CSF is approved clinically to shorten the time of immune recovery following chemotherapy, and the potential for GM-CSF to stimulate anti-tumor responses has been demonstrated in a wide variety of animal models. Efficient drug delivery and effective antigen presentation, however, remain major challenges in its use and are, at least in part, responsible for the failure of systemic administration of GM-CSF to live up to the preclinical promises. Likewise, GM-CSF has been used for treatment of chronic viral hepatitis with positive antiviral effects; however, the ability of systemic administration of GM-CSF to activate the immune system sufficiently to suppress viral replication and eradicate the causative virus has not been achieved.

The present invention includes the design engineering and clinical utility of a lesion-targeted cytokine fusion protein of von Willebrand Factor (vWF) and immunomodulators, such as GM-CSF. This fusion protein can be produced in human cell lines and can effectively deliver a bioactive immunomodulator to tissue lesions, including, for example invasive cancers and infection-induced lesions.

SUMMARY

The present disclosure is based, at least in part, on the development of new fusion polypeptides for the localization of immunological stimulation. The fusion polypeptides can include, e.g., at least an exposed-collagenous (XC-) protein-binding domain (also referred to herein as an "aptamer") sequence, an immunomodulator, and a rigid linker that joins the aptamer sequence and the immunomodulator. The XC-binding aptamer sequence targets (e.g., binds) the polypeptide to the exposed collagen in tissue lesions, such as the lesions caused by cancer, disease, and/or infections. The immunomodulator is then accumulated and localized to the lesion, wherein it modulates the immune system in a targeted manner. This targeting ability minimizes the adverse side effects seen with systemic administration and facilitates the use of lower concentrations of immunomodulators, than when non-targeted immunomodulators are administered systemically. In some cases, the rigid linker improves the specific activity of the fusion polypeptide, when compared to a fusion polypeptide comprising a flexible linker. A rigid linker can be, e.g., a helical linker. In some embodiments, the immunomodulator is a cytokine, such as, e.g., GM-CSF. Also provided herein are methods of treating cancer and/or infectious diseases using the new fusion polypeptides.

In some aspects, the present disclosure provides lesion-targeted fusion polypeptides comprising, consisting, or consisting essentially of (i) an aptamer sequence that binds to exposed collagenous (XC-) proteins, (ii) an immunomodulator, and (iii) a rigid linker that joins the aptamer sequence and the immunomodulator. The rigid linker can be helical. In some cases, the linker comprises an amino acid sequence selected from the group consisting of GAEAAAKEAAAKAG (SEQ ID NO: 9) and AEAAAKEAAAKA (SEQ ID NO: 10). In some aspects, the present disclosure provides lesion-targeted fusion polypeptides comprising, consisting, or consisting essentially of (i) an aptamer sequence that binds to exposed collagenous (XC-) proteins, (ii) an immunomodulator, and optionally (iii) a linker that joins the aptamer sequence and the immunomodulator. The linker can be a rigid linker or a flexible linker. In some cases, the aptamer that binds to the XC-proteins is linked to the N-terminus of the immunomodulator. In some cases, the aptamer that binds to the XC-proteins is linked to the C-terminus of the immunomodulator.

In some embodiments, the aptamer sequence is a polypeptide derived from a propolypeptide of von Willebrand factor (vWFpp) collagen binding domain D2 or a conservative variation thereof that retains collagen binding activity. In some cases, the aptamer sequence comprises an amino acid sequence of ARRGVRVAWREPGRMELNMPHGQE (SEQ ID NO: 1). In some cases, the aptamer sequence comprises an amino acid sequence of RRGVHVGWREPGRMELNMPH (SEQ ID NO: 38).

The immunomodulator can be a cytokine, an interferon, an interleukin, a tumor necrosis factor, a cancer-associated antigen, and a virus-associated antigen. In some cases, the immunomodulator is a cytokine and the cytokine is granulocyte-macrophage colony stimulating factor (GM-CSF) or granulocyte-colony stimulating factor (G-CSF). In some cases, the immunomodulator is an interferon. In some instances, the interferon is INF-α. In some instances, the immunomodulator is an interleukin. In some cases, the interleukin is interleukin-2. In some instances, the immunomodulator is a tumor necrosis factor and is TNF-α. In some cases, the immunomodulator is a cancer-associated antigen. The cancer-associated antigen can be selected from the group consisting of NYESO-1, HER-2, and EGFR. In some instances, the immunomodulator is a virus-associated antigen. In some cases, the virus-associated antigen is associated with herpes simplex virus or adenovirus.

In some embodiments, the cytokine is GM-CSF and comprises the amino acid sequence selected from the group consisting of

```
                                          (SEQ ID NO: 14)
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCATQI
ITFESFKENLKDFLLVIPFDCWEPVQE;

(SEQ ID NO: 29)
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCAIQI
ITFESFKENLKDFLLVIPFDCWEPVQE;
and (SEQ ID NO: 30)
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCATQT
ITFESFKENLKDFLLVIPFDCWEPVQE.
```

In some cases, the fusion polypeptides described herein comprise, consist of, or consist essentially of, from N-terminus to C-terminus (i) an aptamer sequence that binds to exposed collagenous (XC-) proteins, (ii) an immunomodulator, and (iii) a linker that joins the aptamer sequence and the immunomodulator. In some cases, the fusion polypeptides described herein comprise, consist of, or consist essentially of, from C-terminus to N-terminus (i) an aptamer sequence that binds to exposed collagenous (XC-) proteins, (ii) an immunomodulator, and (iii) a linker that joins the aptamer sequence and the immunomodulator.

In some aspects, the present disclosure provides fusion polypeptides comprising an amino acid sequence selected from the group consisting of

```
                                          (SEQ ID NO: 17)
APARSPSPSTQPWEHVNAIQEARRLLNLSRDTAAEMNETVEVISEMFDLQ

EPTCLQTRLELYKQGLRGSLTKLKGPLTMNIASHYKQHCPPTPETSCATQ

IITFESFKENLKDFLLVIPFDCWEPVQEGAEAAAKEAAAKAGARRGVRVA

WREPGRMELNMPHGQE (GM-CSF + Helical Linker + XC-binding domain), (SEQ ID NO: 18)
APARSPSPSTQPWEHVNAIQEARRLLNLSRDTAAEMNETVEVISEMFDLQ

EPTCLQTRLELYKQGLRGSLTKLKGPLTMNIASHYKQHCPPTPETSCATQ

IITFESFKENLKDFLLVIPFDCWEPVQEGSAGSAAGSGARRGVRVAWREP

GRMELNMPHGQE (GM-CSF + Flexible Linker + XC-binding domain), (SEQ ID NO: 19)
METDTLLLWVLLLWVPGSTGHHHHHHHHHHENLYFQGAPARSPSPSTQPW

EHVNAIQEARRLLNLSRDTAAEMNETVEVISEMFDLQEPTCLQTRLELYK

QGLRGSLTKLKGPLTMMASHYKQHCPPTPETSCATQIITFESFKENLKDF

LLVIPFDCWEPVQEGAEAAAKEAAAKAGARRGVRVAWREPGRMELNMPHG

QE (Signal Peptide + His-Tag w/Protease Site +

GM-CSF + Helical Linker + XC-binding domain),
and (SEQ ID NO: 40)
METDTLLLWVLLLWVGSTGHHHEIRREIREIHENLYFQGAPARSPSPSTQ

PWEHVNAIQEARRLLNLSRDTAAEMNETVEVISEMFDLQEPTCLQTRLEL
```

```
-continued
YKQGLRGSLTKLKGPLTMMASHYKQHCPPTPETSCATQIITFESFKENLK

DFLLVIPFDCWEPVQEGSAGSAAGSGARRGVRVAWREPGRMELNMPHGQE (Signal Peptide + His-Tag w/Protease Site + GM- CSF + Flexible Linker + XC-binding domain).
```

In some embodiments, the fusion polypeptides described herein comprise, consist of, or consist essentially of an amino acid sequence selected from the group consisting of

```
                                           SEQ ID NO: 39
METDTLLLWVLLLWVPGSTGHHHHHHHHHHENLYFQGARRGVHVGWREPG

RMELNMPHGGAEAAAKEAAAKAGAPARSPSPSTQPWEHVNAIQEARRLLN

LSRDTAAEMNETVEVISEMFDLQEPTCLQTRLELYKQGLRGSLTKLKGPL

TMMASHYKQHCPPTPETSCATQIITFESFKENLKDFLLVIPFDCWEPVQ

E),
and (SEQ ID NO: 36)
(RRGVHVGWREPGRMELNMPHGGAEAAAKEAAAKAGAPARSPSPSTQPWE

HVNAIQEARRLLNLSRDTAAEMNETVEVISEMFDLQEPTCLQTRLELYKQ

GLRGSLTKLKGPLTMMASHYKQHCPPTPETSCATQIITFESFKENLKDFL

LVIPFDCWEPVQE.
```

In some aspects, the present disclosure provides lesion-targeted fusion polypeptides comprising, consisting, or consisting essentially of (i) an aptamer sequence that binds to exposed collagenous (XC-) proteins, (ii) an immunomodulator, and (iii) at least one linker, wherein the linker joins the aptamer sequence and the immunomodulator or is connected to a terminus of the polypeptide. In some cases, the aptamer sequence is a polypeptide derived from a propolypeptide of von Willebrand factor (vWFpp) collagen binding domain D2 or a conservative variation thereof that retains collagen binding activity. The linker can join the aptamer sequence and the immunomodulator, and can be a rigid linker or a flexible linker.

In some cases, the linker comprises an amino acid sequence selected from the group consisting of GAEAAAKEAAAKAG (SEQ ID NO: 9), AEAAAKEAAAKA (SEQ ID NO: 10), GSAGSAAGSG. (SEQ ID NO: 11), GSAGSAAGSGEF (SEQ ID NO: 12); GSAGSAAGS (SEQ ID NO: 13); GGSG (SEQ ID NO: 20); (D-Arg)-(D-Arg)-GVHVG (SEQ ID NO: 21); GGSGG (SEQ ID NO: 22); SGGSG (SEQ ID NO: 23); GSGSGS (SEQ ID NO: 24); GGSGGSK (SEQ ID NO: 25); GSGGSGGSG (SEQ ID NO: 26); GGSGGSGG (SEQ ID NO: 27); and GGGG (SEQ ID NO: 28). In some embodiments, the aptamer sequence comprises an amino acid sequence of ARRGVRVAWREPGRMELNMPHGQE (SEQ ID NO: 1). In some embodiments, the aptamer sequence comprises an amino acid sequence of RRGVHVGWREPGRMELNMPH (SEQ ID NO: 38).

In some instances, the immunomodulator is selected from the group consisting of a cytokine, an interferon, an interleukin, a tumor necrosis factor, a cancer-associated antigen, and an oncolytic virus-associated antigen. In some cases, the immunomodulator is a cytokine and the cytokine is granulocyte-macrophage colony stimulating factor (GM-CSF) or granulocyte-colony stimulating factor (G-CSF). In some embodiments, the immunomodulator is an interferon. In some embodiments, the interferon is INF-α. In some embodiments, the immunomodulator is an interleukin. In some embodiments, the interleukin is interleukin-2. In some embodiments, the immunomodulator is a tumor necrosis factor and is TNF-α. In some embodiments, the immunomodulator is a cancer-associated antigen. The cancer-associated antigen can be selected from the group consisting of NYESO-1, HER-2, and EGFR. In some embodiments, the immunomodulator is a virus-associated antigen. In some embodiments, the virus-associated antigen is associated with herpes simplex virus or adenovirus.

In some embodiments, the fusion polypeptides described herein further comprise a purification tag. The purification tag can be a cleavable Histidine-tag. In some embodiments, the fusion polypeptides described herein further comprise an export signal peptide. The export signal peptide can be a murine IgG kappa-chain signal peptide.

In some embodiments, the fusion polypeptide is glycosylated. In some embodiments, the fusion polypeptide is amidated. In some embodiments, the fusion polypeptide is PEGylated.

In some aspects, the present disclosure provides a vector comprising, consisting of, or consisting essentially of a nucleic acid sequence that encodes any of (e.g., any one of the) fusion polypeptides described herein, wherein the nucleic acid sequence is optimized for expression in an expression system selected from the group consisting of: *E. coli*, yeast, and mammalian gene expression systems.

In some aspects, the present disclosure provides a pharmaceutical composition comprising any of (e.g., any one of) the fusion polypeptides described herein and a pharmaceutically acceptable carrier.

In some aspects, the present disclosure provides a method of treating an infection in a subject, e.g., treating infected tissue in a subject, e.g., wherein the infection is characterized at least in part by exposed collagen being present in, on, and/or in close proximity to the infected tissue, the method comprising, consisting of, or consisting essentially of administering to a subject in need of such treatment a fusion polypeptide comprising (i) an aptamer sequence that binds to exposed collagenous (XC-) proteins and (ii) an immunomodulator, in an amount sufficient to treat the infection. In some cases, the fusion polypeptide further comprises (iii) at least one linker, wherein the linker joins the aptamer sequence and the immunomodulator or is connected to a terminus of the polypeptide. In some cases, the linker is a rigid linker and joins the aptamer sequence and the immunomodulator. The linker can comprise, consist of, or consist essentially of an amino acid sequence selected from the group consisting of GAEAAAKEAAAKAG (SEQ ID NO: 9) and AEAAAKEAAAKA (SEQ ID NO: 10).

In some embodiments of the methods described herein, the aptamer sequence is a polypeptide derived from a propolypeptide of von Willebrand factor (vWFpp) collagen binding domain D2 or a conservative variation thereof that retains collagen binding activity. The linker can comprise, consist of, or consist essentially of an amino acid sequence selected from the group consisting of GAEAAAKEAAAKAG (SEQ ID NO: 9), AEAAAKEAAAKA (SEQ ID NO: 10), GSAGSAAGSG. (SEQ ID NO: 11), GSAGSAAGSGEF (SEQ ID NO: 12); GSAGSAAGS (SEQ ID NO: 13); GGSG (SEQ ID NO: 20); (D-Arg)-(D-Arg)-GVHVG (SEQ ID NO: 21); GGSGG (SEQ ID NO: 22); SGGSG (SEQ ID NO: 23); GSGSGS (SEQ ID NO: 24); GGSGGSK (SEQ ID NO: 25); GSGGSGGSG (SEQ ID NO: 26); GGSGGSGG (SEQ ID NO: 27); and GGGG (SEQ ID NO: 28). In some cases, the aptamer sequence comprises an amino acid sequence of ARRGVRVAWREPGRMELNMPHGQE (SEQ ID NO: 1). In some cases, the aptamer sequence comprises an amino acid sequence of RRGVHVGWREPGRMELNMPH (SEQ ID NO: 38).

In some embodiments, the infection, e.g., of tissue in a subject, is selected from the group consisting of a viral infection, a bacterial infection, a protozoal infection, and a fungal infection. The infection can be characterized at least in part by exposed collagen being present in, on, and/or in close proximity to the infected tissue, e.g., in a lesion caused by the infection. In some cases, the infection is a viral infection and the virus is selected from the group consisting of hepatitis, human immunodeficiency virus (HIV, e.g., HIV-1), and herpesvirus (e.g., HHV-8). In some cases, the method further comprises administering an anti-viral agent. In some cases, the virus is hepatitis and is hepatitis C. In some cases, the infection is a bacterial infection and the bacteria is tuberculosis. In some cases, the methods further comprise administering an anti-bacterial agent. In some cases, the infection is a protozoal infection and the protozoa is mycoplasma or chlamydia. In some cases, the methods further comprise administering an anti-protozoal agent. In some cases, the infection is a fungal infection and the fungus is aspergillus. In some cases, the methods further comprise administering an anti-fungal agent.

In some embodiments of the methods described herein, the immunomodulator is selected from the group consisting of a cytokine, an interferon, an interleukin, a tumor necrosis factor, a cancer-associated antigen, and an oncolytic virus-associated antigen. In some cases, the immunomodulator is a cytokine and the cytokine is granulocyte-macrophage colony stimulating factor (GM-CSF) or granulocyte-colony stimulating factor (G-CSF). The GM-CSF can comprise, consist of, or consist essentially of the amino acid sequence selected from the group consisting of

```
                                        (SEQ ID NO: 14)
APARSPSPSTQPWEHVNAIQEARRLLNLSRDTAAEMNETVEVISEMFDLQ
EPTCLQTRLELYKQGLRGSLTKLKGPLTMNIASHYKQHCPPTPETSCATQ
IITFESFKENLKDFLLVIPFDCWEPVQE;

(SEQ ID NO: 29)
APARSPSPSTQPWEHVNAIQEARRLLNLSRDTAAEMNETVEVISEMFDLQ
EPTCLQTRLELYKQGLRGSLTKLKGPLTMNIASHYKQHCPPTPETSCAIQ
IITFESFKENLKDFLLVIPFDCWEPVQE;
and (SEQ ID NO: 30)
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCATQT
ITFESFKENLKDFLLVIPFDCWEPVQE.
```

In some aspects, the present disclosure provides methods of treating an infection in a subject, e.g., treating infected tissue in a subject, comprising administering to a subject in need of such treatment a fusion polypeptide comprising the amino acid sequence selected from the group consisting of

```
                                        (SEQ ID NO: 17)
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQEGAEAAAKEAAAKAGARRGVRVAW

REPGRMELNMPHGQE (GM-CSF + Helical Linker + XC-binding domain),
```

-continued (SEQ ID NO: 18)
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQEGSAGSAAGSGARRGVRVAWREPG

RMELNMPHGQE (GM-CSF + Flexible Linker + XC-binding domain), (SEQ ID NO: 19)
METDTLLLWVLLLWVPGSTGHHHHHHHHHHENLYFQGAPARSPSPSTQPW

EHVNAIOEARRLLNLSRDTAAEMNETVEVISEMFDLQEPTCLQTRLELYK

QGLRGSLTKLKGPLTMMASHYKQHCPPTPETSCATQIITFESFKENLKDF

LLVIPFDCWEPVQEGAEAAAKEAAAKAGARRGVRVAWREPGRMELNMPHG

QE (Signal Peptide + His-Tag w/Protease Site +

GM-CSF + Helical Linker + XC-binding domain), (SEQ ID NO: 36)
METDTLLLWVLLLWVPGSTGHHHHHHHHHHENLYFQGARRGVHVGWREPG

RMELNMPHGGAEAAAKEAAAKAGAPARSPSPSTQPWEHVNAIQEARRLLN

LSRDTAAEMNETVEVISEMFDLQEPTCLQTRLELYKQGLRGSLTKLKGPL

TMMASHYKQHCPPTPETSCATQIITFESFKENLKDFLLVIPFDCWEPVQ

E;

(SEQ ID NO: 39)
RRGVHVGWREPGRMELNMPHGGAEAAAKEAAAKAGAPARSPSPSTQPWEH

VNAIQEARRLLNLSRDTAAEMNETVEVISEMFDLQEPTCLQTRLELYKQG

LRGSLTKLKGPLTMMASHYKQHCPPTPETSCATQIITFESFKENLKDFLL

VIPFDCVVEPVQE;
and (SEQ ID NO: 40)
METDTLLLWVLLLWVPGSTGHHHHHHHHHHENLYFQGAPARSPSPSTQPV

VEHVNAIQEARRLLNLSRDTAAEMNETVEVISEMFDLQEPTCLQTRLELY

KQGLRGSLTKLKGPLTMMASHYKQHCPPTPETSCATQIITFESFKENLKD

FLLVIPFDCWEPVQEGSAGSAAGSGARRGVRVAWREPGRMELNMPHGQE (Signal Peptide + His-Tag w/Protease Site + GM- CSF + Flexible Linker + XC-binding domain).

In some aspects the present disclosure provides methods of treating cancer in a subject, e.g., cancerous tissue (.e.g., cancerous tissue having exposed collagen in, on, and/or around the cancerous tissue), the methods comprising, consisting of, or consisting essentially of administering to a subject in need of such treatment a fusion polypeptide comprising (i) an aptamer sequence that binds to exposed collagenous (XC-) proteins, (ii) an immunomodulator, and (iii) at least one linker, wherein the linker is a rigid linker and joins the aptamer sequence and the immunomodulator, in an amount sufficient to treat the cancer. In some embodiments, the cancer comprises a tumor. In some cases, the methods further comprise administering an anti-cancer agent to the subject.

In some aspects the present disclosure provides methods of treating cancer (e.g., cancerous tissue) in a subject, comprising, consisting of, or consisting essentially of administering to a subject in need of such treatment the pharmaceutical compositions described herein, in an amount sufficient to treat the cancer. In some cases, the methods further comprise administering an anti-cancer agent to the subject. In some cases of the methods described herein, the aptamer sequence is a polypeptide derived from a propolypeptide of von Willebrand factor (vWFpp) collagen binding domain D2 or a conservative variation thereof that retains collagen binding activity. In some embodiments, the linker comprises an amino acid sequence of GAEAAAKEAAAKAG (SEQ ID NO: 9) or AEAAAKEAAAKA (SEQ ID NO: 10). In some cases, the aptamer sequence comprises an amino acid sequence of ARRGVRVAWREPGRMELNMPHGQE (SEQ ID NO: 1). In some cases, the aptamer sequence comprises an amino acid sequence of RRGVHVGWREPGRMELNMPH (SEQ ID NO: 38).

In some embodiments of the methods described herein, the immunomodulator is selected from the group consisting of a cytokine, an interferon, an interleukin, a tumor necrosis factor, a cancer-associated antigen, and an oncolytic virus-associated antigen. In some embodiments, the immunomodulator is a cytokine and the cytokine is granulocyte-macrophage colony stimulating factor (GM-CSF) or granulocyte-colony stimulating factor (G-CSF). In some cases, the GM-CSF comprises the amino acid sequence selected from the group consisting of (SEQ ID NO: 14)
APARSPSPSTQPWEHVNAIQEARRLLNLSRDTAAEMNETVEVISEMFDLQ
EPTCLQTRLELYKQGLRGSLTKLKGPLTMNIASHYKQHCPPTPETSCATQ
IITFESFKENLKDFLLVIPFDCWEPVQE;

(SEQ ID NO: 29)
APARSPSPSTQPWEHVNAIQEARRLLNLSRDTAAEMNETVEVISEMFDLQ
EPTCLQTRLELYKQGLRGSLTKLKGPLTMNIASHYKQHCPPTPETSCAIQ
IITFESFKENLKDFLLVIPFDCWEPVQE;
and (SEQ ID NO: 30)
APARSPSPSTQPWEHVNAIQEARRLLNLSRDTAAEMNETVEVISEMFDLQ
EPTCLQTRLELYKQGLRGSLTKLKGPLTMMASHYKQHCPPTPETSCATQT
ITFESFKENLKDFLLVIPFDCWEPVQE.

As used herein, the term "patient" or "subject" is used throughout the specification to describe an animal, human or non-human, rodent or non-rodent, to whom treatment according to the methods of the present invention is provided. Veterinary and non-veterinary applications are contemplated. The term includes but is not limited to birds, reptiles, amphibians, and mammals, e.g., humans, monkeys and other primates, pigs, rodents such as mice and rats, rabbits, guinea pigs, hamsters, cows, horses, cats, dogs, sheep and goats. Preferred subjects are humans (adult, juvenile, or neonate), farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 is a schematic showing an XC-binding GM-CSF/vWF fusion protein. Murine signal peptide (green); 10×His-Tag with protease site (grey); GM-CSF cytokine (gold); linker (blue); vWF-derived XC-binding domain (red).

FIG. 2A is a schematic of a vWF-Derived XC-protein binding polypeptide.

FIG. 2B is a picture showing in vitro binding of the XC-binding sequences, along with extended leader and trailing flanking sequences.

FIG. 2C is a picture showing in vivo fluorescence imaging of the XC-binding constructs in a live mouse.

FIG. 2D is a picture showing in vivo fluorescence imaging of the XC-binding constructs in a tumor xenograft.

FIG. 3 is a panel of two pictures of gels showing the expression and purification of a GM-CSF/vWF fusion protein.

DETAILED DESCRIPTION

Figure 4A:
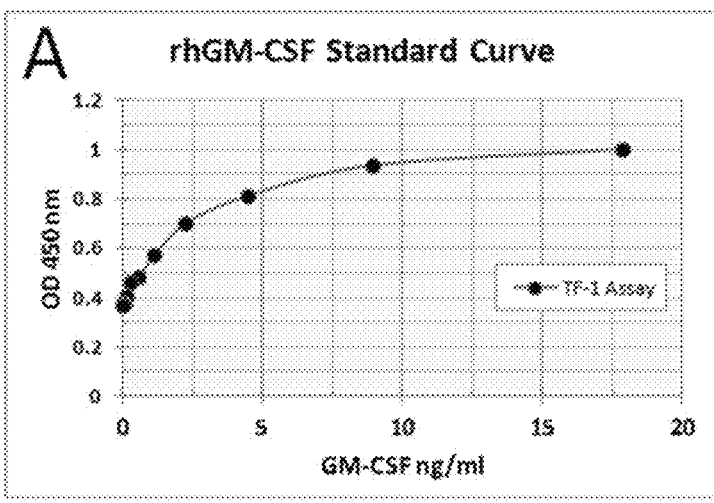
FIG. 4A is a graph showing the concentration-dependent biological activity of a clinical-grade pharmaceutical control GM-CSF.

The present disclosure is based, at least in part, on the development of new fusion polypeptides that, at least, provide an immunomodulator and specifically target the immunomodulator to tissue lesions, using the exposed collagenous protein-binding activity of an XC-binding aptamer. The present disclosure is also based, in part, on localized immunological stimulation using new fusion polypeptides for the treatment of cancer and/or infectious diseases. The fusion polypeptides can include, for example, (i) an exposed collagenous (XC-) protein-binding aptamer for pro-active lesion targeting, (ii) an immunomodulator for immunological stimulation, and (iii) at least one linker. The linker can be a rigid linker, e.g., a rigid helical linker. The immunomodulator can be, for example, a cytokine (e.g., GM-CSF, G-CSF, etc.), interferons (e.g., INF-α, INF-β, INF-γ, etc.), interleukins (e.g., IL-2, IL-7, IL-12, IL-15, IL-18, IL-21, etc.), tumor necrosis factors (e.g., TNF-α, etc.), cancer-associated antigens (e.g., NYESO-1, HER-2, EGRS, etc.), or virus-associated antigens (e.g., antigens associated with infectious viruses, for example hepatitis viruses (e.g., hepatitis C virus), herpes simplex virus, adenovirus, human immunodeficiency virus, measles virus, Cowpox virus, Vaccinia virus, etc.). The XC-targeted immunomodulator polypeptides described herein provide a novel approach to immunotherapy (e.g, cytokine immunotherapy) with the design engineering, genetic engineering, and bio-manufacturing of a lesion-targeted fusion immunomodulator. The fusion polypeptides can be administered by simple intravenous infusion, and they specifically seek-out and accumulate-in the tumor compartments of invasive cancers and the lesions of chronic infections. This enables clinical efficacy to be consistently achieved at lower immunomodulator doses with less adverse systemic side effects in the clinic. Additionally, in some cases, the rigid linker improves the specific activity of the fusion polypeptide.

In many disease-induced lesions, including both invasive metastatic cancer nodules and the lesions of chronic viral hepatitis, the physiological and pharmacological challenge is one of marshalling the relevant cytokine-activated immune cells into the same compartment as the target antigens, which are present within the respective lesions. To address this problem, the present invention includes, inter alia, the development of a suitable lesion-targeted cytokine delivery system that can efficiently deliver systemically administered recombinant immunomodulators, such as GM-CSF, to the respective lesions, wherein the lesion-targeted cytokine can recruit and activate immune cell effectors to the presence of the respective antigens. The current invention describes the genetic engineering of a recombinant fusion protein that transposes a high-affinity collagen-binding functionality, which is inherent within the complex structure of von Willebrand Factor propeptide (vWFpp), to provide a clinically useful gain-of-function (i.e., lesion targeting) to recombinant human GM-CSF, which is thereby targeted selectively and efficiently to significant histological lesions. In this "designer" cytokine fusion protein, human GM-CSF is physically linked in an optimized manner to a vWF-derived protein binding domain/aptamer that binds with high affinity to (i.e., is selective for) abnormally exposed collagenous (XC-) proteins that are a common histopathological property of, for example, invasive cancers or the lesions that are characteristic of viral hepatitis. By targeting abnormal XC-proteins, a common histopathological property of the tumor microenvironment, rather than a specific phenotypic property of the dynamic cancer cells, the XC-binding aptamer overcomes a major problem of tumor heterogeneity, while still targeting the disease-induced lesion.

Selective Targeting of Immunomodulators to Lesion and/or Tumor Microenvironment (TME)

Neoplastic lesions do not only comprise malignant cancer cells but also include stromal components such as fibroblasts, endothelial cells, and inflammatory cells. An opportunistic tumor microenvironment is formed by those components and promotes tumorigenesis, tumor progression and metastasis. Although cancer drug development traditionally focused on targeting the cancer cell and its cell division cycle, emphasis has recently shifted toward the tumor microenvironment for novel therapeutic and prevention strategies (See Sounni and Noel, Clinical Chem., 59:85-93, 2013; Fang and DeClerck, Cancer Res., 73:4965-4977, 2013). The process of tumor invasion, metastasis, angiogenesis, and reactive stroma formation disrupts normal tissue histology and leads to pathologic exposure of collagenous proteins (XC-) within the tumor microenvironment, e.g., in, on, and/or around the cancerous tissue. Thus, the abnormal exposure of collagenous proteins is a characteristic histopathologic property of all neoplastic lesions.

Similarly, infections, such as bacterial, fungal and viral infections can create tissue lesions that lead to the pathologic exposure of XC-proteins. Selective targeting of therapeutic agents to these lesion microenvironments enables the targeting of drugs to the exposed collagenous proteins of the lesion and/or in the close vicinity of neighboring cancer cells, rather than targeting the rapidly evolving cancer and virus-infected cells per se. The targeting of this common histopathologic property of lesions, as in the novel fusion proteins described herein, can enable the localization and accumulation of immunomodulators in the diseased/cancerous tissues upon intravenous infusion (conventional IV administration). Other examples of polypeptides including the XC targeting domain or aptamer are known in the art (including, for example, U.S. Pat. No. 6,955,898, WO 2016/054107, Hall et al., Hum Gene Ther 11:983-993, 2000; Gordon et al., Cancer Res. 60:3343-3347, 2000; Hall et al., Intl J Mol Med 6:635-643, 2000; Gordon et al., Expert Opin Biol Ther 10:819-832, 2010; Gordon et al., Int'l J Oncol 36:1341-1353, 2010; Chawla et al., Mol Ther 2009; 17(9): 1651-7; Chawla et al., Mol Ther 2010; 18:435-441, which are all incorporated herein in their entirety).

Provided herein are novel fusion polypeptides that target immunomodulators to pathological areas of exposed collagenous proteins. The fusion polypeptides described herein include at least three domains: (i) an aptamer sequence that binds to exposed collagenous (XC) proteins and (ii) an immunomodulator, and (iii) at least one linker. The XC-binding function is derived from the D2 domain of the propolypeptide of vWF, which has been purposefully altered in amino acid sequence to preclude the formation of Cys-Cys disulfide bonds (Takagi et al., A Collagen/gelatin-binding decapeptide derived from bovine propolypeptide of von Willebrand Factor. Biochemistry, 1992, 31:8530-8534, Tuan, T. L., et al., Conn. Tiss. Res. 34:1-9, 1996; Gordon, E. M., et al., Hum. Gene Ther. 8:1385-1394; U.S. Pat. No. 6,387,663, all herein incorporated by reference). von Willebrand factor was initially identified as a hemostatic factor in studies of inherited hemophilias (Wagner, Ann. Rev. Cell. Biol. 6:217, 1990), and has been shown to perform a vital surveillance function by targeting platelet aggregates to injured/diseased tissues and vascular lesions (Ginsburg and Bowie, Blood 79:2507-2519, 1992). Several collagen-binding aptamer sequences are known in the art (Cruz M A, et al., J. Biol. Chem., 270:10822-10827, 1995; Hoylaerts, M. F., et al., Biochem. J., 324:185-191, 1997; Lankhof, H., et al., Thrombos Haemostas, 75:950-958, 1996, which are incorporated herein in their entirety).

In some embodiments, the aptamer sequence that binds to exposed collagenous (XC-) proteins comprises an amino acid sequence of ARRGVRVAWREPGRMELNMPHGQE (SEQ ID NO: 1); CAGRGVRVAWREPGRCELNCPKG (SEQ ID NO: 4); CARRGVHVGWREPSFCALSCPHG (SEQ ID NO: 5); CARRGVHVGWREPGRMELNMPHG (SEQ ID NO: 6); WREPSFMALS (SEQ ID NO: 7); WREPGRMELN (SEQ ID NO: 8); RRGVHVGWREPSFMALSMPHG (SEQ ID NO: 32); RRGVHVGWREPGRMELNMPH (SEQ ID NO: 38); or RRGVRVAWREPGRMELNMPHG (SEQ ID NO: 33). Skilled practitioners will appreciate that variations in these sequences are possible and such variants may be useful in the present invention. Accordingly, sequences having at least 70%, e.g., at least 80%, 90%, or at least 99% identity to SEQ ID NOs.: 1, 4, 5, and/or 6 can be utilized. In some embodiments flanking regions on the terminus of the aptamer sequence enhance binding specificity and/or affinity. In some embodiments, the aptamer sequence is derived from the human vWF propolypeptide collagen binding domain D2 comprising the amino acid sequence of PLPYLRNCRYDVCSCSDGRECLCGALASYAAACAGRGVRVAWREPGRCELNCPK GQVYLQCGTPCNLTCRSLSYPDEECNEACLEGCFCPPGLYMDERGDCVPKAQCP CYYDGEIFQPED (SEQ ID NO: 2). In some embodiments, the aptamer sequence is derived from the bovine vWF propolypeptide collagen binding domain D2 comprising the amino acid sequence of ILTSPKFEACHSAVSPLPYLRNCRYDVCACSDGRDCLCDAVANYAAACARRGVH VGWREPSFCALSCTHGQVYQQCGTPCNLTCRSLSHPDEECTEVCLEGCFCPPGLF LDETGSCVPKA (SEQ ID NO: 3). A skilled practitioner could appreciate that variations on these sequences, parts of these sequences, and/or variations of parts of these sequences may be useful in the present invention, while maintaining the exposed collagenous protein-binding activity. In some embodiments, the aptamer sequence comprises between 10 and 25 amino acids, e.g., 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, 22 amino acids, 23 amino acids, 24 amino acids, 25 amino acids, at least 10 amino acids, up to 25 amino acids, and/or less than 25 amino acids. In some embodiments, the between 10 and 25 amino acids of the aptamer sequence comprise at least an amino acid sequence of SEQ ID NO: 7 or SEQ ID NO: 8.

In some embodiments, the fusion polypeptides described herein can also be used, e.g., for imaging and/or tracking primary and/or metastatic tumors in a subject. For example, the aptamer sequence can be labeled with a detectable moiety, such as a radioactive isotope, a magnetic compound, an x-ray absorber, a fluorescent molecule, a chemical compound, and/or a biological tag. After administering the labeled fusion polypeptides to a subject, the fusion polypeptide is targeted to the primary and metastatic tumors and/or lesions in the subject through its collagen binding aptamer sequence. Lesions and/or tumors can then be detected using computed tomography, radiography, magnetic resonance imaging, laser scanning microscopy, immunohistochemistry, fluorescent microscopy, Raman spectroscopy, optical coherence tomography (OCT), detection of radiation (e.g., x-ray) scattering or absorption, ultrasound, and/or isotope detection. Practitioners will appreciate that determining the dose to be administered to the subject for imaging or tracking is within the skill of the practitioner and will depend upon the type and location of the lesion(s) and/or tumor(s) in the patient, the type of detectable moiety to be used, and the type of imaging to be performed. In some embodiments the labeled fusion polypeptide comprises the sequence of RRGVHVGWREPSFMALSMPHGGSGK-(FITC) (SEQ ID NO: 34) or RRGVRVAWREPGRMELNMPHGGSGK-(FITC) (SEQ ID NO: 35).

Immunomodulating Agents

Immunomodulators are a group of drugs that affect the immune system, e.g., drugs that induce, stimulate, enhance, or suppress an immune response. A non-limiting list of immunomodulators includes: cytokines, interleukins, interferons, tumor necrosis factors, immunomodulatory imide drugs, cancer-associated antigens, oncolytic virus-associated antigens, and synthetic polymers. The efficacy of immunomodulators is often limited by systemic side effects, due to their non-selective activity towards the immune system. As described herein, the side effects of immunomodulators can be reduced by directly targeting immunomodulators to the primary and secondary sites of infection/disease, for examples the disease-induced lesions. Such selective lesion targeting can enhance the immune response, stimulate white blood cell production, and the recruit and activate phagocytic cells, antigen-presenting cells, dendritic cells, and natural killer T cells.

GM-CSF is a potent immuno-stimulatory cytokine with multiple functions of interest in cancer immunotherapy: including the stimulation of white blood cell production, and the recruitment and activation of phagocytic cells, antigen-presenting cells, dendritic cells, and natural killer T cells. Indeed, GM-CSF has been reported to exhibit significant antitumor activity as a single agent when injected directly into metastatic lesions (Ridolfi et al., Intralesional granulocyte-monocyte colony-stimulating factor followed by subcutaneous interleukin-2 in metastatic melanoma: A pilot study in elderly patients. J. Eur. Acad. Dermatol. Venereol. 2001, 15: 218-223, which is incorporated herein in its entirety), and the systemic administration of GM-CSF has confirmed its ability to enhance the immune responses and promote tumor rejection in both preclinical and clinical studies (Jager et al., Granulocyte-macrophage-colony-stimulating factor enhances immune responses to melanoma-associated peptides in vivo. Int. J Cancer, 1996, 67:54-62; and Lee and Margolin, Cytokines in Cancer Immunotherapy. Cancers, 2011, 3:3856-3893, which are incorporated herein in their entirety). Given the rapid blood clearance of GM-CSF and the lack of tumor specificity, however, the high GM-CSF doses that are required to activate an immune response within the tumor compartments are associated with severe side effects and toxicities that currently limit its therapeutic use by systemic administration (Ruef and Coleman. Granulocyte-macrophage colony-stimulating factor: pleiotropic cytokine with potential clinical usefulness. Rev Infect Dis. 1990, 12:41-62; and Arellano and Lonial, Clinical uses of GM-CSF, a critical appraisal and update. Biologics: Targets & Therapy 2008, 2:13-27, which are incorporated herein in their entirety). The invention described herein overcomes the dose-limiting toxicities of systemic GM-CSF administration by providing "active" lesion-targeting, as an enabling gain-of-function, in an unique and innovative manner.

The fusion polypeptides described herein can comprise an immunomodulator selected from the group consisting of cytokines, interleukins, interferons, tumor necrosis factors, cancer-associated antigens, and virus-associated antigens. These fusion polypeptides can include, for example, a recombinant cytokine. The cytokine, for example, can be GM-CSF and can comprise an amino acid sequence selected from the group consisting of SEQ ID NOs: 14, 19, or 30. Skilled practitioners will appreciate that variations in such sequences may be possible, while retaining immune-stimulating activity. Accordingly, sequences having at least 70%, e.g., at least 80%, 90%, 95%, or at least 99%, identity to SEQ ID NOs: 14, 19, or 30 can be utilized. The interleukin can be, for example, interleukin-2. The interferon can be, for example, INF-α. The tumor necrosis factor can be, for example, TNF-α. The cancer-associated antigen can be, for example, selected from the group consisting of NYESO-1, HER-2, and EGFR. The virus-associated antigen can be, for example, associated with an oncolytic virus-associated antigen, associated with herpes simplex virus or associated with adenovirus.

The effect of cytokines or other immunomodulators on the immune system are known in the art, and can include, for example, stimulation of proliferation, differentiation, the activation and tracking of effector CD4+ and CD8+ T lymphocytes and natural killers; the stimulation of proliferation and differentiation of progenitor cells of the hematopoietic system, causing the formation of cells such as granulocytes, macrophages/monocytes and T lymphocytes; and the stimulation of synthesis by the immune cells of IFN-γ and immunoglobulins (Yuzhakova, D. V, et al., "Immunotherapy of Cancer (Review)" CTM 2016; vol. 8. No. 1 pages 173-181, which is incorporated herein in its entirety). Cytokines can also reduce the vascularization of the tumor which can reduce the immunosuppression of the tumor and increase immunogenicity of the tumor cells.

Linking Domains of Novel Fusion Polypeptides

In some embodiments, the fusion polypeptides described herein further include at least one linker (e.g., spacers). These linkers join the functional domains of the fusion polypeptide (e.g., the aptamer sequence that binds to XC-proteins and the immunomodulator). These linkers position the functional domains for optimal activity, spacing, flexibility, and/or interaction. In some embodiments, these linkers can be rigid and/or helical, restricting the flexibility/movement between the functional binding domains. In some cases, these rigid linkers increase the specific activity of the polypeptide. In some embodiments, these linkers can add flexibility, reducing the steric hindrances between the functional binding domains. The fusion polypeptides described herein have at least one linker comprising an amino acid sequence such as SEQ ID NO: 9, SEQ ID NO: 10, SEQ ID NO: 11, SEQ ID NO: 12, SEQ ID NO: 13, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, GSGK (SEQ ID NO: 31), or variants of these sequences. Examples of a rigid linker include a linker comprising an amino acid sequence such as SEQ ID NOs: 9 or 10. In some embodiments, a fusion polypeptide comprising a rigid helical linker has an improved specific activity, when compared to a fusion polypeptide comprising a flexible linker. In some embodiments, the linker is a glycine and/or serine rich sequence.

Figures 1, 2A, 2B:
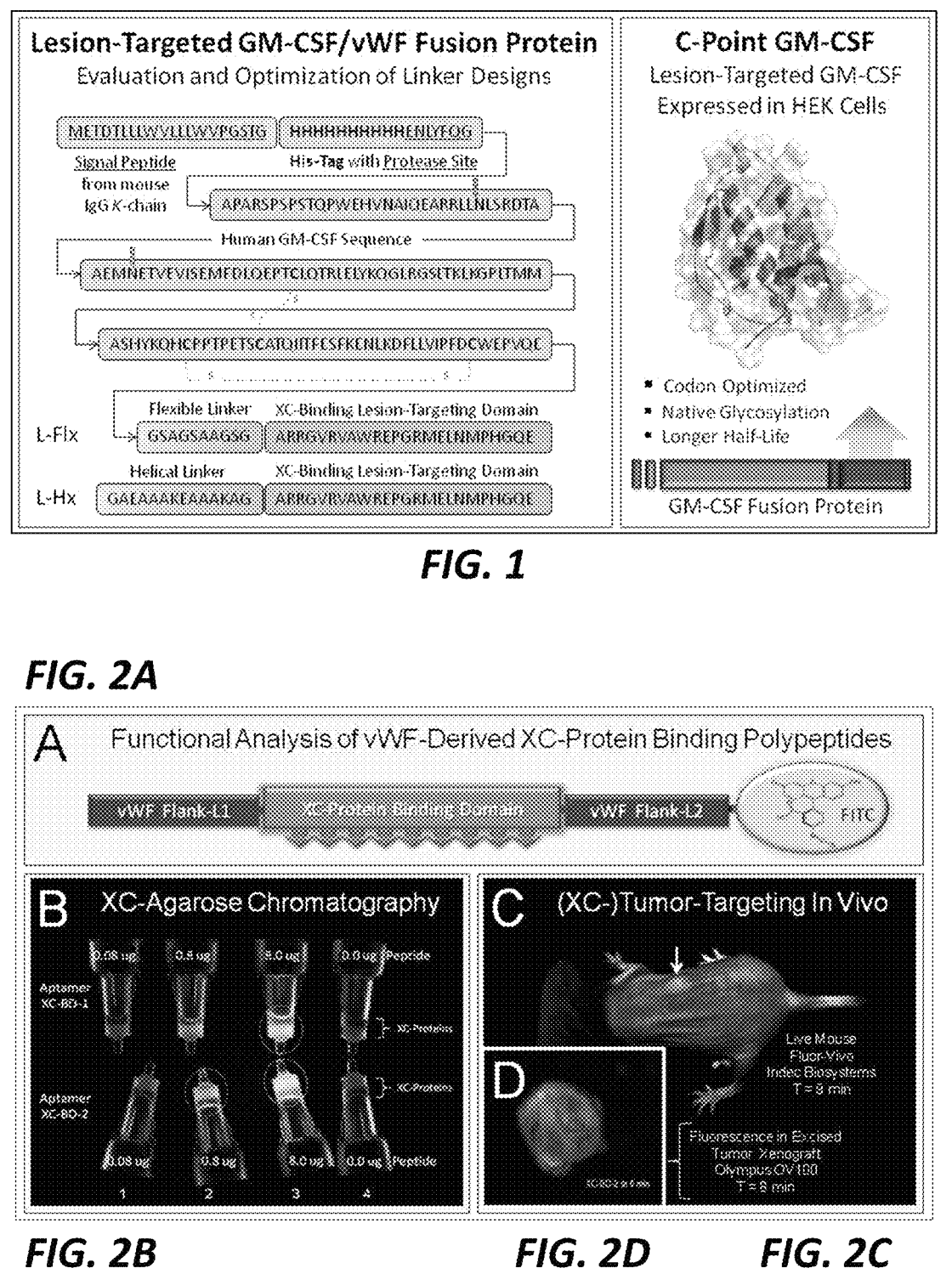

As described herein, the XC-targeted fusion polypeptides comprise multiple functional domains with the following non-limiting structural features: (i) the coding sequence for an immunomodulator; (ii) a vWF-derived XC-binding aptamer sequence; (iii) a rigid helical linker or a flexible unstructured linker that joins (i) and (ii); optionally (iv) an export signal peptide; and optionally (v) a cleavable purification tag. More specifically, the XC-targeted fusion cytokine polypeptide can comprise: (i) the natural N-terminal export signal peptide of human GM-CSF is replaced by the murine IgG kappa-chain signal peptide to enable higher level expression in human cells; (ii) a N-terminal His-tag flanked by a TEV-protease site to facilitate XC-targeted GM-CSF purification from cell culture supernatants; (iii) the coding sequences for mature (proteolytically processed) human GM-CSF; (iv) either a rigid helical linker or a flexible unstructured linker designed to separate the cytokine and XC-binding domains, while minimizing steric hindrances, and (v) the vWF-derived XC-binding domain (see FIG. 1). In some embodiments, the immunomodulator (e.g., GM-CSF) is linked to the N-terminus of the XC-binding aptamer sequence. In some embodiments, the immunomodulator (e.g., GM-CSF) is linked to the C-terminus of the XC-binding aptamer sequence. In some embodiments, the aggregates of coding sequences are subjected to codon optimization (e.g., avoiding cis-acting sequence motifs, AT-rich or GC-rich sequence stretches, cryptic donor and acceptor splice sites, repeat sequences, and RNA secondary structures that would impair gene expression). Such optimization creates a synthetic gene construct that is capable of high-level expression and secretion in human cell cultures. Following gene expression and secretion in serum-free cell culture medium, the fusion protein (sans signal peptide) can be purified from the cell culture medium to yield a functional fusion polypeptide. Purification can be performed using, for example, Ni-affinity chromatography, followed by site-specific cleavage of the N-terminal His-tag by TEV-protease, which is removed in a final chromatography step, yielding the bifunctional XC-targeted fusion cytokine in purified form.

The fusion polypeptides can be acetylated, amidated, and/or PEGylated at N- or C-terminus. Alternatively or in addition, D-amino acids can be included. Inclusion of D-amino acids, acetylation, amidation, and/or PEGylation increase the stability of the fusion polypeptides and make them more resistant to proteolysis.

Generation of the Fusion Polypeptides

A fusion polypeptide described herein can be produced by expression of a recombinant nucleic acid encoding the polypeptides or by chemical synthesis (e.g., by solid-phase synthesis or other methods well known in the art, including synthesis with an ABI peptide synthesizer; Applied Biosystems, Foster City, Calif.). For example, a fusion polypeptide can be produced by expression of a nucleic acid encoding the protein in prokaryotes. These include but are not limited to microorganisms such as bacteria transformed with recombinant bacteriophage DNA, plasmid DNA or cosmid DNA expression vectors encoding a fusion protein of the invention. The constructs can be expressed in *E. coli* in large scale for in vitro assays. Purification from bacteria is simplified when the sequences include tags for one-step purification by nickel-chelate chromatography. The construct can also contain a tag to simplify isolation of the fusion polypeptide. For example, a polyhistidine tag of, e.g., six histidine residues, can be incorporated at the amino terminal end of the fluorescent protein. The polyhistidine tag allows convenient isolation of the protein in a single step by nickel-chelate chromatography. The fusion polypeptides described herein can also be engineered to contain a cleavage site to aid in protein recovery. Alternatively, the fusion polypeptides described herein can be expressed directly in a desired host cell for assays in situ.

When the host is an eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptides of the invention, and a second foreign DNA molecule encoding a selectable phenotype, such as the herpes simplex thymidine kinase gene. Another method is to use an eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, an eukaryotic host is utilized as the host cell as described herein.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and WI38.

For long-term, high-yield production of recombinant proteins, stable expression can be used. Rather than using expression vectors which contain viral origins of replication, host cells can be transformed with the cDNA encoding a fusion protein of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in $tk^-$, $hgprt^-$ or $aprt^-$ cells respectively. Also, antimetabolite resistance can be used as the basis of selection for dhfr, which confers resistance to methotrexate (Wigler, et al., Proc. Natl. Acad. Sci USA, 77:3567, 1980; O'Hare, et al, Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (omithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

With the fusion polypeptide (e.g., GM-CSF/vWF) gene construct optimized for expression in human cells, as described herein, the fusion polypeptide is correctly folded, native protein produced by transiently transfected mammalian cells, using an advanced expression system and conditions to obtain high expression yields. In previous studies, the genetic engineering of antibody-cytokine fusion proteins, referred to generically as immunocytokines, has been hampered by issues of species specificity, poor protein expression, fusion protein immunogenicity, target validation, inadvertent biodistribution, and natural tumor heterogeneity. The present invention provides for, at least, an optimized lesion-targeted immunomodulator fusion polypeptide for high expression and efficient purification.

The secreted fusion protein can be purified using affinity chromatography via an auxiliary, cleavable 10×His-tag, which can be removed by proteolytic processing (e.g., subsequent to purification). In some embodiments, the affinity chromatography is followed by an additional purification step, yielding the highly-purified fusion polypeptide.

The complete coding sequences for the lesion-targeted fusion polypeptide, including the immunomodulator (e.g., human GM-CSF) sequences, designated linker sequences, and human vWF-derived lesion-targeting sequences, can be "codon-optimized"—changed to that utilized by highly-expressed human genes, without changing any amino acid—to further enable high-level expression in transfected human producer cells. Clinical preparations of rGM-CSF can be produced in E. coli and S. cerevisiae. In some embodiments, the lesion-targeted fusion cytokine is expressed in human (HEK293) producer cells, which ensures the proper folding, posttranslational processing, and secretion of the therapeutic protein with native human glycosylation, which further serves to improve the stability and half-life of the therapeutic cytokine (Marini et al., Recombinant human granulocyte-macrophage colony-stimulating factor: effect of glycosylation on pharmacokinetic parameters. Electronic Journal of Biotechnology. 2007, 10:271-278; and Zhang et al., Synthesis of granulocyte—macrophage colonystimulating factor as homogeneous glycoforms and early comparisons with yeast cell-derived material. Proc Natl Acad Sci USA, 2014, 111: 2885-2890, which are incorporated herein in their entirety).

In one embodiment of the immunomodulator lesion-targeted polypeptide, such as a cytokine/vWF fusion protein, human GM-CSF is linked to an XC-binding domain of the vWF-derived polypeptide by an optimized linker. The resulting XC-targeting fusion cytokine can be efficiently expressed in human "producer cell" lines, producing a properly folded and naturally glycosylated polypeptide that exhibits the improved pharmacokinetics and pharmacodynamics of bifunctionality: (i) XC-binding for lesion targeting and (ii) GM-CSF bioactivity for localized immunological stimulation. A skilled practitioner would appreciate that additional design considerations are considered when optimizing the fusion polypeptides described herein. Such considerations include, but are not limited to, the known structure-function relationships of GM-CSF expression, posttranslational processing, secretion, and bioactivity; the variety of XC-binding sequences derived from vWF; the intricate "loop" structure of the vWF D2 domain; the minimization of cysteine residues in the vWF D2 domain; the highly-conserved vWF structural XC-binding and flanking motifs across different species; and experimental determination of the precise vWF derived XC-binding aptamer sequences. The fusion polypeptides described herein are designed to be optimal for use in vivo for active and efficient lesion targeting upon intravenous administration.

Pharmaceutical Compositions, Dosage Regimen, and Methods of Administration

Provided herein are also pharmaceutical compositions comprising one or more of the fusion polypeptides described herein. The compositions can further include one or more therapeutic and/or biologic agents known in the art to be effective in treating diseases and/or infections, i.e., an anti-cancer agent, an anti-viral agent, an anti-fungal agent, or an anti-bacterial agent. Such pharmaceutical compositions can be used to treat cancer and/or infections as described herein. In some embodiments, the pharmaceutical composition is administered to a subject in need of treatment intravenously or subcutaneously.

The active ingredient of the pharmaceutical compositions described herein can be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. A pharmaceutical composition provided herein can include another delivery agent and a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compositions can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Certain tumors and/or infections may be accessible by administration by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the therapeutic polypeptides can be prepared with carriers that will protect the therapeutic polypeptides against rapid elimination from the body, such as a controlled release formulation, including implants and microencapsulated delivery systems.

In some embodiments, the pharmaceutical compositions can be directly administered to the areas of active angiogenesis or infection. In some embodiments, the pharmaceutical composition can be administered through conventional routes, e.g., intravenously. Microencapsulation technology or liposomes can be used to protect the pharmaceutical compositions during circulation and release them at the site of active angiogenesis or infection.

The pharmaceutical compositions can be included in a container, pack, or dispenser together with instructions for administration.

The therapeutic and/or biologic compositions can be administered in an effective amount, at dosages and for periods of time necessary to achieve the desired result. An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of the new polypeptides disclosed herein. See e.g., Physicians' Desk Reference, 63rd edition, Thomson Reuters, Nov. 30, 2008. For example, Dosage, toxicity and therapeutic efficacy of the pharmaceutical compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Polypeptides which exhibit high therapeutic indices are preferred. While compounds that exhibit toxic side effects may be used, the present invention provides for a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any polypeptide used in the method of the invention, the therapeutically effective dose can be estimated initially from cell culture assays. A dose may be formulated in animal models to achieve a circulating plasma concentration range that includes the IC50 (i.e., the concentration of the test protein which achieves a half-maximal inhibition of symptoms) as determined in cell culture. Such information can be used to more accurately determine useful doses in humans. Levels in plasma may be measured, for example, by high performance liquid chromatography.

Kits

Also provided are kits that include one or more of the fusion polypeptides described herein. Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can include at least one (e.g., one, two, three, four, five, or more) compositions containing at least one (e.g., one, two, three, four, five, or more) of the fusion polypeptides described herein, and at least one (e.g., one, two, three, four, five, or more) other composition in a separate vial containing a therapeutic or biologic agent known in the art to be effective in treating cancer and/or an infection.

Compositions and kits as provided herein can be used in accordance with any of the methods (e.g., treatment methods) described herein. For example, compositions and kits can be used to treat cancer or can be used to treat fungal, bacterial, and/or viral infections. Those skilled in the art will be aware of other suitable uses for compositions and kits provided herein, and will be able to employ the compositions and kits for such uses.

Methods of Use of the Fusion Polypeptides.

The fusion polypeptides and pharmaceutical compositions described herein can be useful for the treatment of a disease, for example, cancer, disease, and/or infections. The cancer can be, e.g., a primary or metastatic cancer, including but not restricted to, colorectal cancer, breast cancer, brain tumors, non-small cell lung cancer, pancreatic cancer, prostate cancer, sarcoma, carcinoma, and/or melanoma. The cancer can be, e.g., cancer of the stomach, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and/or throat; sarcoma, or choriocarcinoma. In some embodiments, the cancer is a solid tumor, for example, a sarcoma, a carcinoma, or a melanoma.

In general, the methods of treating cancer can include administering to a subject having cancer an amount of the fusion polypeptide or pharmaceutical composition sufficient to treat cancer in the patient. An exemplary method of treating cancer in a subject using the fusion polypeptide can include: (a) providing an fusion polypeptide and (b) administering to a subject in need of treatment an effective amount of a pharmaceutical composition comprising the fusion polypeptide. In some embodiments, the method of treating cancer further comprises administering an anti-cancer agent to the subject in need of treatment. Administration of an anti-cancer agent can be concurrent or in sequence with the administration of the fusion polypeptide. In some embodiments, the subject is a human.

The infection can be, e.g., a bacterial infection, fungal infection, protozoal, and/or a viral infection. The bacterial infection can be, but is not limited to, tuberculosis, *Salmonella typhi*, staphylococcal, streptococcal, clostridia, bacillus anthrax, syphilis, gonorrhea, other gram-positive bacteria, other gram-negative bacteria, etc. Protozoal infections include but are not limited to, mycoplasma and Chlamydia. The viral infection can be, but is not limited to an infection by hepatitis, human immunodeficiency virus (e.g., HIV-1), herpesvirus (e.g., HHV-8), or parvovirus. The fungal infection can be, but is not limited to, aspergillus and candida. In general, the methods of treating infections can include administering to a subject having an infection an amount of the fusion polypeptide or pharmaceutical composition sufficient to treat the infection in the patient. An exemplary method of treating an infection in a subject using the fusion polypeptide can include: (a) providing a fusion polypeptide and (b) administering to a subject in need of treatment an effective amount of a pharmaceutical composition comprising the fusion polypeptide. In some embodiments, the method of treating an infection further comprises administering to the subject in need of treatment an agent known in the art to treat the infection (e.g., an anti-bacterial agent, an anti-fungal agent, or an anti-viral agent). Administration of an agent known in the art to treat the infection can be concurrent or in sequence with the administration of the fusion polypeptide. In some embodiments, the subject is a human.

EXAMPLES

The invention is further described in the following examples, which do not limit the scope of the invention described in the claims.

Example 1. Optimization of the Fusion Polypeptide

The rhGM-CSF/vWF fusion protein was designed and codon-optimized for expression in human HEK 293 cells. The primary structure of this optimized protein is shown in the left panel of FIG. 1. The high-performance murine signal peptide (green)(METDTLLLWVLLLWVPGSTG (SEQ ID NO: 16)) and a cleavable 10×His purification tag (grey) (HHHHHHHHHHENLYFQG (SEQ ID NO: 15)) were removed during protein expression and purification, respectively, leaving the mature GM-CSF cytokine (gold)(APARSPSPSTQPWEHVNAIQEARRLLNLSRDTAAEMNETVEVISEMFDLQEPTCL
QTRLELYKQGLRGSLTKLKGPLTMMASHYKQHCPPTPETSCATQIITFESFKENL KDFLLVIPFDCWEPVQE (SEQ ID NO: 14)), which is connected/fused with an experimentally-determined linker sequence (blue)(Flexible Linker, GSAGSAAGSG (SEQ ID NO: 11)) (Helical Linker, GAEAAAKEAAAKAG (SEQ ID NO: 9)) to the C-terminal vWF-derived XC-targeting domain (red) (ARRGVRVAWREPGRMELNMPHGQE (SEQ ID NO: 1)).

Example 2. Optimization of the Collagen-Binding Sequence

To further optimize (XC-) lesion targeting sequences for the GM-CSF fusion cytokine, strategic vWF-derived XC-binding sequences, along with extended leader and trailing flanking sequences (see FIG. 2A), were compared in a series of in vitro binding studies (FIG. 2B). Selected constructs were further validated in vivo in an animal model of cancer (FIG. 2C, FIG. 2D). The vWF-derived XC-binding constructs comprised the minimal XC-binding decapeptide (SEQ ID NO: 7 or SEQ ID NO: 8), N- and C-terminal flacking residues, and a C-terminal linker (for example, SEQ ID NO: 31). XC-BD-1 comprises the vWR-derived sequence from bovine vWR, for example RRGVHVGWREPSFMALSMPHGGSGK-(FITC) (SEQ ID NO: 34) and XC-BD-2 comprises the vWR-derived sequence from human vWR, for example RRGVRVAWREPGRMELNMPHGGSGK-(FITC) (SEQ ID NO: 35).

FIG. 2A and FIG. 2B illustrate the multiple features that went into the design of the fusion polypeptides described herein in order to optimize production and clinical applications, including, e.g., the genetic engineering for high-level expression, the advanced linker design improves performance, the codon-optimization for human producer cells, proper folding enhances bio-production yields, native glycosylation improves pharmacology, and cleavable His-Tag facilitates APA purification Example 3. Generation of Tumor-Targeting and Viral Lesion Targeting Fusion Polypeptides Protein Expression in Human Producer Cells: produced the authentic human GM-CSF cytokine with correct post-translational modifications, folding, secretion, stability, and specific activity. Native glycosylation is known to be important for minimizing immunogenicity, as well as optimizing GM-CSF bioactivity, half-life, and receptor binding (Cebon et al., 1990, J. Biol. Chem. 265, 4483-4491).

The CM-CSF/vWF gene construct was optimized for expression in human cells, subcloned into the pcDNA 3.4 expression vector, and the native protein, correctly folded and naturally glycosylated, was produced by transient transfection of mammalian cells in suspension culture. Using an advanced expression system and optimized polypeptide design, high expression yields were obtained. HEK 293 cells were grown in shake flasks as suspension cultures in chemically-defined serum-free medium, and high level recombinant protein expression was initiated by transient transfection.

Figure 3:
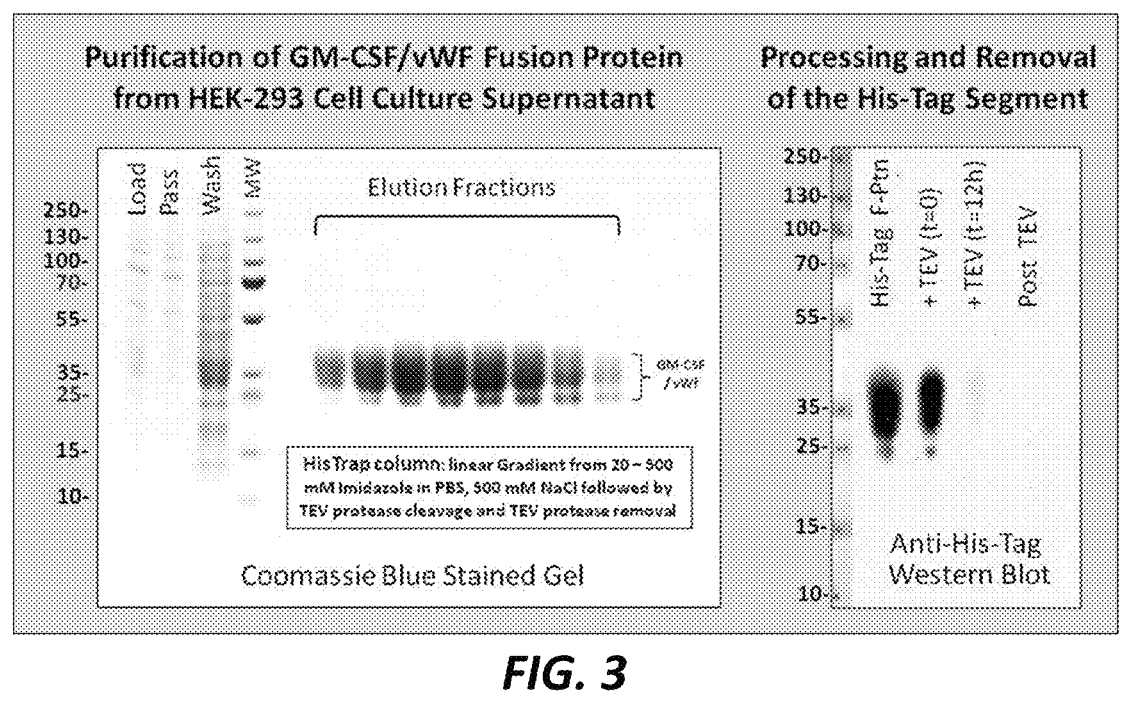

The secreted mature recombinant protein was purified from cell culture supernatant using metal chelate chromatography via the auxiliary, cleavable 10×His-tag, which is subsequently removed by proteolytic processing, followed by an additional purification step, yielding the highly-purified protein API. Detailed documentation of the production includes a Coomassie Blue stained PAGE gel (left panel of FIG. 3) and a Western blot (right panel of FIG. 3).

Example 4: Validation of GM-CSF/vWF Fusion Peptide Bioactivity

Evaluation of the specific activity of the purified GM-CSF/vWF fusion proteins was performed under standardized conditions (TF-1 Cell Proliferation Assay), using clinical grade rhGM-CSF as a Control. The resulting Dose Response Curves confirmed that both recombinant fusion proteins were biologically active in stimulating TF-1 cell proliferation by receptor-mediated mechanisms. It was further determined that the rigid (helical) linker design was superior to the flexible linker, in terms of specific activity (see FIG. 4B and FIG. 4C), confirming that this elegant design engineering provided more optimal spacing and orientation of the two functional components. While somewhat less active than the clinical grade standard (ED/EC 50=2 ng/ml vs 4.6 ng/ml [mol/mol]), this small (expected) decrease in pharmacodynamics is more than offset by the larger gains in pharmacokinetics and local biodistribution by virtue of the pro-active tumor-targeting functionality.

Figure 4B:
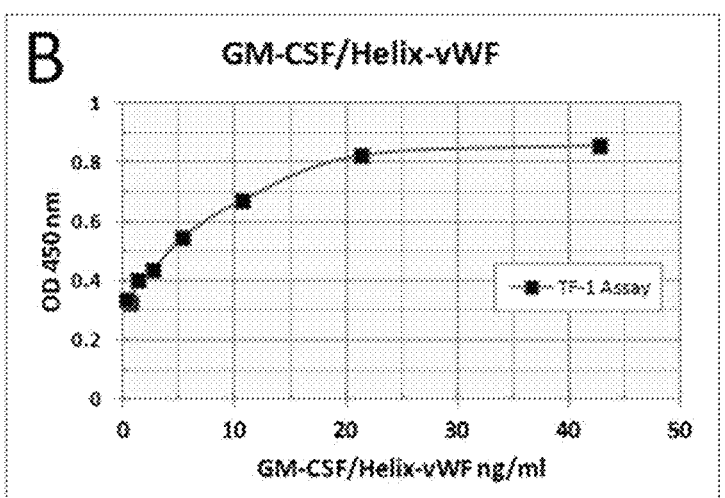
FIG. 4B is a graph showing the concentration-dependent biological activity of a lesion-targeted GM-CSF fusion protein with a rigid helical linker ("GM-CSF/Helix-vWF").
Figure 4C:
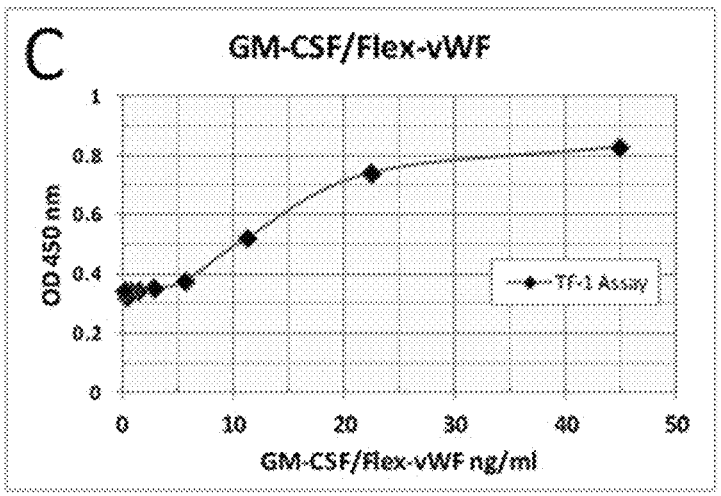
FIG. 4C is a graph showing the concentration-dependent biological activity of a lesion-targeted GM-CSF fusion protein with a flexible linker ("GM-CSF/Flex-vWF").

Dose/Response Curves for two experimental variants of the XC-targeted GM-CSF/vWF fusion protein were compared with that of a clinical-grade pharmaceutical control GM-CSF (FIG. 4A). The incorporation of a rigid helical linker in GM-CSF/Helix-vWF (FIG. 4B) was determined to be twice as potent as the construct incorporating a flexible linker, GM-CSF-Flex (FIG. 4C)—hence emphasizing that successful design engineering with steric hindrances and resulting pharmacodymanic effects in mind is non-obvious, necessitating an experimental approach.

Example 5. Optimization and Validation of FP-III Construct Bioactivity and XC-Binding The FP-III (FPIII) fusion protein was designed and codon-optimized for expression in human and/or mammalian producer cells (e.g., transfected human HEK cells). (e.g., GGCAGCACCGGCCACCACCATCACCATCAC-CACCATCATCACGAGAACCTGT ATTTT-CAAGGCGCCAGACGGGGCGTGCACGTGG-GATGGCGGGAACCCGGCA GAATGGAACTGAACATGCCCCACGGCG-GAGCCGAGGCCGCTGCCAAAGAAG CCGCTGCTAAAGCCGGCGCTCCCGCCAGAA GCCCTAGCCCTTCTACCCAGCC CTGGGAGCACGT-GAACGCCATCCAGGAAGCCAGACGGCTGCT-GAACCTGAG CCGGGACACAGCCGCCGAGAT-GAACGAGACAGTGGAAGTGATCAGCGAGAT GTTCGATCTGCAAGAACCTACCTGCCTGCA-GACCCGGCTGGAACTGTACAAG CAGGGCCTGCGGGGCAGCCTGACCAAGCT-GAAGGGCCCCCTGACCATGATGG CCAGCCACTA-CAAGCAGCACTGCCCCCCCACCCCCGA-GACAAGCTGCGCCAC CCAGATCATCACCTTCGAGAGCTT-CAAAGAGAACCTGAAGGACTTCCTGCTG GTGATCCCCTTCGACTGCTGGGAGCCCGTGCAG-GAATGATGAGAATTC (SEQ ID NO: 37)). This construct was designed placing the XC-binding aptamer closer to the N-terminal (e.g., on the N-terminal) than the C-terminal end of the mature fusion protein (e.g., closer than the immunomodulator to the N-terminal end of the fusion protein). In some constructs the XC-binding aptamer sequence is closer to the C-terminal (e.g., on the C-terminal) end of the fusion protein. The primary structure of this optimized protein is signal peptide—His-tag with protease—XC-binding aptamer—helical linker—GM-CSF (METDTLLLWVLLL-WVPGSTGHREIHHHHEIHHEN-LYFQGARRGVHVGWREPGR MELNMPHG-GAEAAAKEAAAKAGAPARSPSPSTQPWEHV NAIQEARRLLNLSRD TAAEMNETVE-VISEMFDLQEPTCLQTRLELYKQGLRGSLTKLKG-PLTMMASHYK QHCPPTPETSCATQIITFESFKENLKD-FLLVIPFDCWEPVQE (SEQ ID NO: 36)). In some cases the fusion protein comprises an XC-binding aptamer, a helical linker, and GM-CSF.

Binding of the FPIII construct to XC(collagen III)-agarose was measured using recombinant constructs labeled with a fluorescent green fluorochrome. Recombinant GMCSF proteins were labeled with Alexa-Fluor 488 and purified from the dye front by size-exclusion column chromatography. The rigid helix linker in the Helix and FP-III constructs provided for increased binding to XC-agarose. Note: possible steric hindrances of the fluorochrome.

Figure 5:
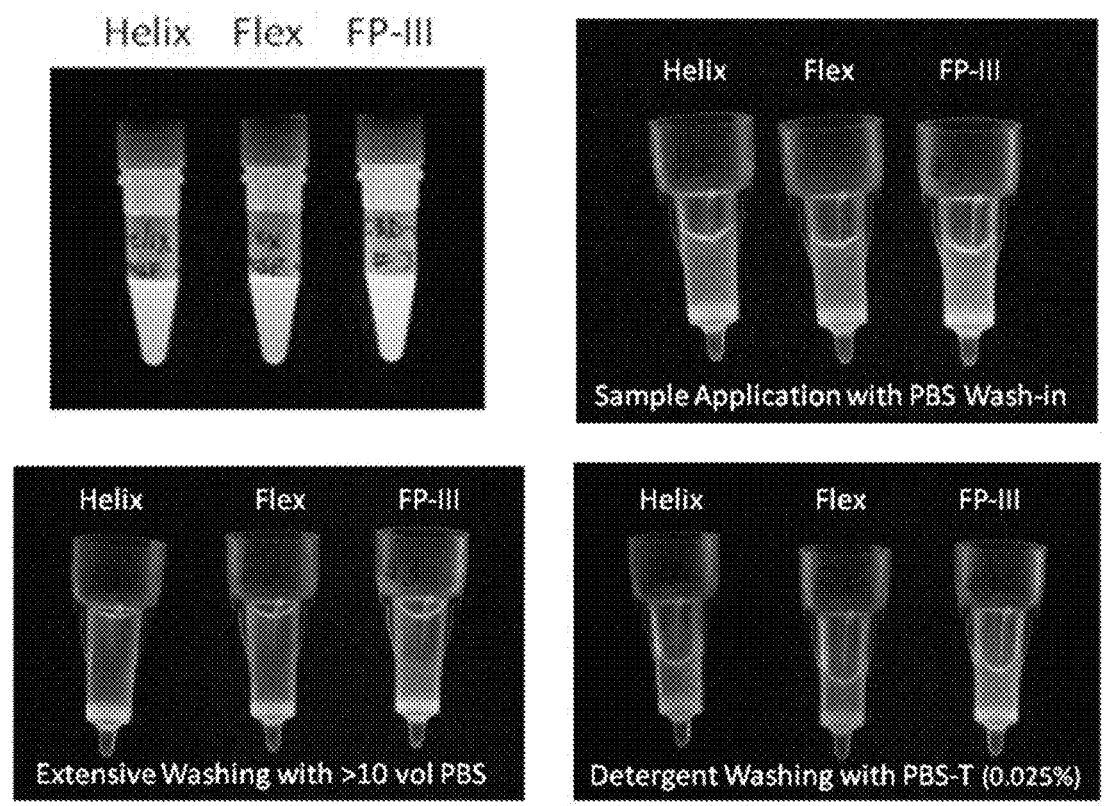
FIG. 5 is a panel of images showing a comparative collagen-agarose binding assay using the rXC-GMCSF constructs.

In this experiment (see FIG. 5) each of the 3 recombinant XC-GM-CSF fusion constructs were labeled with a fluorescent green fluorochrome, and the purified fluorescent proteins were applied to separate collagen-aragose columns, followed by washing under increasingly stringent conditions (e.g., Sample application with PBS wash-in, extensive washing with >10 vol PBS, and detergent washing with PBS-T (0.025%)). The FPIII construct exhibits increased binding and retention upon stringent washing.

Figure 6A:
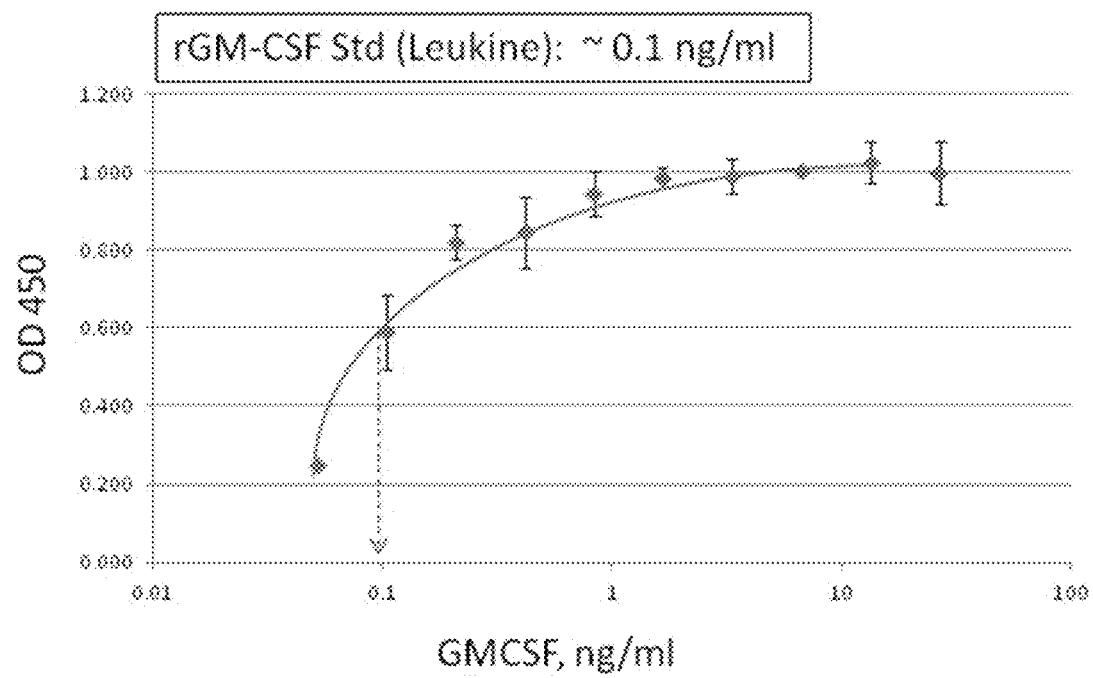
FIG. 6A is a graph showing bioactivity of rGM-CSF.
Figure 6B:
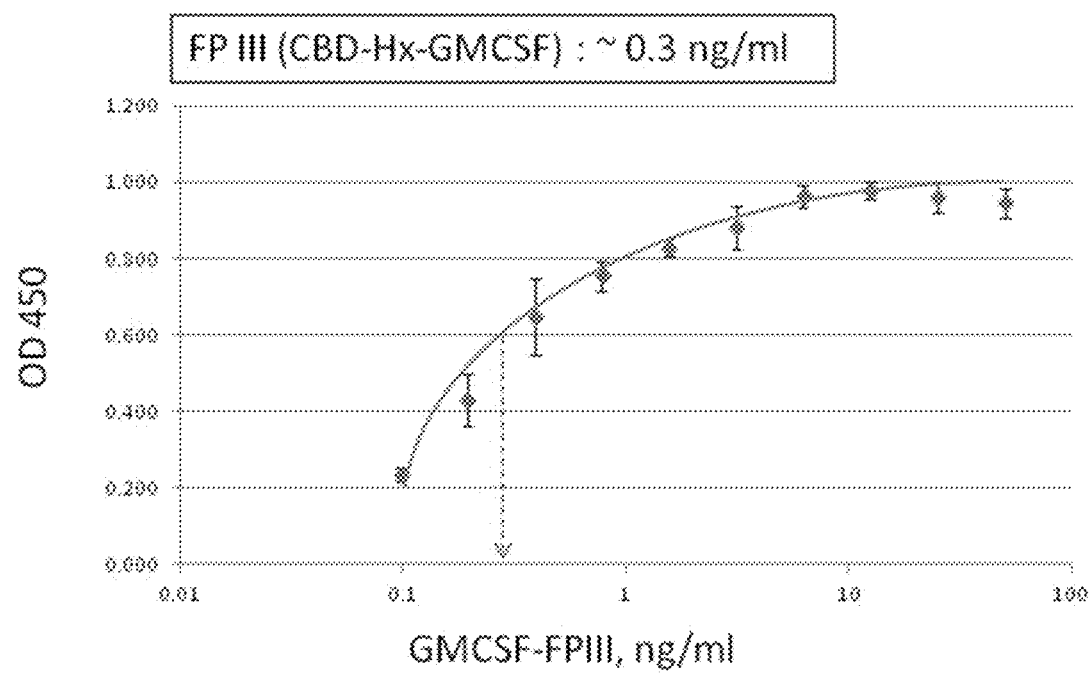
FIG. 6B is a graph showing bioactivity of FP-III construct (CBD-Hx-GMCSF).

Evaluation of the activity of purified XC-binding aptamer+Helical Linker+GM-CSF construct (FP-III) (e.g., SEQ ID NO: 36)(see FIG. 6B) was performed using rGM-CSF (Leukine) as a control (see FIG. 6A). The activity of the fusion proteins described herein can be measured using methods known in the art and described herein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A lesion-targeted fusion polypeptide comprising an amino acid sequence selected from the group consisting of:

(SEQ ID NO: 17)
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQEGAEAAAKEAAAKAGARRGVRVAW

REPGRMELNMPHGQE;

(SEQ ID NO: 18)
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQEGSAGSAAGSGARRGVRVAWREPG

RMELNMPHGQE;

(SEQ ID NO: 19)
METDTLLLWVLLLWVPGSTGHHHEIRRHIRRHENLYFQGAPARSPSPSTQ

PWEHVNAIQEARRLLNLSRDTAAEMNETVEVISEMFDLQEPTCLQTRLEL

YKQGLRGSLTKLKGPLTMMASHYKQHCPPTPETSCATQIITFESFKENLK

DFLLVIPFDCWEPVQEGAEAAAKEAAAKAGARRGVRVAWREPGRMELNMP

HGQE;

(SEQ ID NO: 40)
METDTLLLWVLLLWVPGSTGHHHHIRRHIRRHENLYFQGAPARSPSPSTQ

PWEHVNAIQEARRLLNLSRDTAAEMNETVEVISEMFDLQEPTCLQTRLEL

YKQGLRGSLTKLKGPLTMMASHYKQHCPPTPETSCATQIITFESFKENLK

DFLLVIPFDCWEPVQEGSAGSAAGSGARRGVRVAWREPGRMELNMPHGQ

E;

(SEQ ID NO: 36)
METDTLLLWVLLLWVPGSTGHHHHIRRHIRRHENLYFQGARRGVHVGWRE

PGRMELNMPHGGAEAAAKEAAAKAGAPARSPSPSTQPWEHVNAIQEARRL

LNLSRDTAAEMNETVEVISEMFDLQEPTCLQTRLELYKQGLRGSLTKLKG

PLTMMASHYKQHCPPTPETSCATQIITFESFKENLKDFLLVIPFDCWEPV

QE;
and (SEQ ID NO: 39)
RRGVHVGWREPGRMELNMPHGGAEAAAKEAAAKAGAPARSPSPSTQPWEH

VNAIQEARRLLNLSRDTAAEMNETVEVISEMFDLQEPTCLQTRLELYKQG

LRGSLTKLKGPLTMMASHYKQHCPPTPETSCATQIITFESFKENLKDFLL

VIPFDCWEPVQE.

2. The fusion polypeptide of claim 1, further comprising a purification tag or an export signal peptide.

3. A pharmaceutical composition comprising the fusion polypeptide of claim 1 and a pharmaceutically acceptable carrier.

4. The lesion-targeted fusion polypeptide of claim 1, wherein the amino acid sequence is:
APARSPSPSTQPWEHVNAIQEARRLLNLSRDTAAEMNETVEVISEMFDLQEPTCL QTRLELYKQGLRGSLTKLKGPLTMMASHYKQHCPPTPETSCATQIITFESFKENLKDFLL VIPFDCWEPVQEGAEAAAKEAAAKAGARRGVRVAWREPGRMELNMPHGQE (SEQ ID NO: 17).

5. The fusion polypeptide of claim 4, further comprising a purification tag or an export signal peptide.

6. A pharmaceutical composition comprising the fusion polypeptide of claim 4 and a pharmaceutically acceptable carrier.

7. The lesion-targeted fusion polypeptide of claim 1, wherein the amino acid sequence is:
APARSPSPSTQPWEHVNAIQEARRLLNLSRDTAAEMNETVEVISEMFDLQEPTCL QTRLELYKQGLRGSLTKLKGPLTMMASHYKQHCPPTPETSCATQIITFESFKENLKDFLL VIPFDCWEPVQEGSAGSAAGSGARRGVRVAWREPGRMELNMPHGQE (SEQ ID NO: 18).

8. The fusion polypeptide of claim 7, further comprising a purification tag or an export signal peptide.

9. A pharmaceutical composition comprising the fusion polypeptide of claim 7 and a pharmaceutically acceptable carrier.

10. The lesion-targeted fusion polypeptide of claim 1, wherein the amino acid sequence is:
METDTLLLWVLLLWVPGSTGHHHHHHHHHHENLYFQGAPARSPSPSTQPWEHV NAIQEARRLLNLSRDTAAEMNETVEVISEMFDLQEPTCLQTRLELYKQGLRGSLTKLKG PLTMMASHYKQHCPPTPETSCATQIITFESFKENLKDFLLVIPFDCWEPVQEGAEAAAKE AAAKAGARRGVRVAWREPGRMELNMPHGQE (SEQ ID NO: 19).

11. The fusion polypeptide of claim 10, further comprising a purification tag or an export signal peptide.

12. A pharmaceutical composition comprising the fusion polypeptide of claim 10 and a pharmaceutically acceptable carrier.

13. The lesion-targeted fusion polypeptide of claim 1, wherein the amino acid sequence is:
METDTLLLWVLLLWVPGSTGHHHHHHHHHHENLYFQGAPARSPSPSTQPWEHV NAIQEARRLLNLSRDTAAEMNETVEVISEMFDLQEPTCLQTRLELYKQGLRGSLTKLKG PLTMMASHYKQHCPPTPETSCATQIITFESFKENLKDFLLVIPFDCWEPVQEGSAGSAAG SGARRGVRVAWREPGRMELNMPHGQE (SEQ ID NO: 40).

14. The fusion polypeptide of claim 13, further comprising a purification tag or an export signal peptide.

15. A pharmaceutical composition comprising the fusion polypeptide of claim 13 and a pharmaceutically acceptable carrier.

16. The lesion-targeted fusion polypeptide of claim 1, wherein the amino acid sequence is:

METDTLLLWVLLLWVPGSTGHHHHHHHHHHEN-LYFQGARRGVHVGWREPGR MELNMPHG-GAEAAAKEAAAKAGAPARSPSPSTQP-WEHVNAIQEARRLLNLSRDTAAE MNETVEVISEMFDLQEPTCLQTRLE-LYKQGLRGSLTKLKGPLTMMASHYKQHCPPT-PET SCATQIITFESFKENLKDFLL-VIPFDCWEPVQE (SEQ ID NO: 36).

17. The fusion polypeptide of claim 16, further comprising a purification tag or an export signal peptide.

18. A pharmaceutical composition comprising the fusion polypeptide of claim 16 and a pharmaceutically acceptable carrier.

19. The lesion-targeted fusion polypeptide of claim 1, wherein the amino acid sequence is:

RRGVHVGWREPGRMELNMPHG-GAEAAAKEAAAKAGAPARSPSPSTQPWEHVN AIQEARRLLNLSRDTAAEMNETVE-VISEMFDLQEPTCLQTRLE-LYKQGLRGSLTKLKGPL TMMASHYKQHCPPT-PETSCATQIITFESFKENLKDFLLVIPFDCWEPVQE (SEQ ID NO: 39).

20. The fusion polypeptide of claim 19, further comprising a purification tag or an export signal peptide.

21. A pharmaceutical composition comprising the fusion polypeptide of claim 19 and a pharmaceutically acceptable carrier.

\* \* \* \* \*

UNITED STATES PATENT AND TRADEMARK OFFICE
CERTIFICATE OF CORRECTION

PATENT NO.        : 10,913,779 B2
APPLICATION NO.   : 15/880434
DATED             : February 9, 2021
INVENTOR(S)       : Hall et al.

Page 1 of 1

It is certified that error appears in the above-identified patent and that said Letters Patent is hereby corrected as shown below:

In the Claims

On Column 47, Line 30, In Claim 1, delete "GHHHEIRRHIRRH" and insert
-- GHHHHHHHHHH --, therefor.

On Column 47, Line 40, In Claim 1, delete "GHHHHIRRHIRRH" and insert
-- GHHHHHHHHHH --, therefor.

On Column 47, Line 48, In Claim 1, delete "GHHHHIRRHIRRH" and insert
-- GHHHHHHHHHH --, therefor.

On Column 48, Line 17, In Claim 4, delete "CL QT" and insert -- CLQT --, therefor.

On Column 48, Line 31, In Claim 7, delete "CL QT" and insert -- CLQT --, therefor.

On Column 48, Line 44, In Claim 10, delete "HV NA" and insert -- HVNA --, therefor.

On Column 48, Line 59, In Claim 13, delete "HV NA" and insert -- HVNA --, therefor.

On Column 49, Line 7, In Claim 16, delete "GR ME" and insert -- GRME --, therefor.

On Column 49, Line 12, In Claim 16, delete "ET SC" and insert -- ETSC --, therefor.

On Column 49, Line 25, In Claim 19, delete "PL TM" and insert -- PLTM --, therefor.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*